(12) United States Patent
Griebenow et al.

(10) Patent No.: US 11,077,111 B2
(45) Date of Patent: Aug. 3, 2021

(54) USE OF FUSED HETEROAROMATIC PYRROLIDONES FOR TREATMENT AND PREVENTION OF DISEASES IN ANIMALS

(71) Applicant: Bayer Animal Health GmbH, Leverkusen (DE)

(72) Inventors: Nils Griebenow, Dormagen (DE); Maria De Lourdes Mottier, Langenfeld (DE); Gerald Beddies, Leverkusen (DE); Jörg Cramer, Wermelskirchen (DE); Ulf Bömer, Glienicke (DE); Iring Heisler, Düsseldorf (DE)

(73) Assignee: Bayer Animal Health GmbH, Leverkusen (DE)

( * ) Notice: Subject to any disclaimer, the term of this patent is extended or adjusted under 35 U.S.C. 154(b) by 0 days.

(21) Appl. No.: 16/757,083

(22) PCT Filed: Oct. 15, 2018

(86) PCT No.: PCT/EP2018/078086
§ 371 (c)(1),
(2) Date: Apr. 17, 2020

(87) PCT Pub. No.: WO2019/076817
PCT Pub. Date: Apr. 25, 2019

(65) Prior Publication Data
US 2020/0261461 A1 Aug. 20, 2020

(30) Foreign Application Priority Data
Oct. 19, 2017 (EP) .................................. 17197344.9

(51) Int. Cl.
*A61K 31/519* (2006.01)
*A61P 37/08* (2006.01)
*A61K 31/437* (2006.01)

(52) U.S. Cl.
CPC .......... *A61K 31/519* (2013.01); *A61K 31/437* (2013.01); *A61P 37/08* (2018.01)

(58) Field of Classification Search
CPC .................................................... C07D 471/04
See application file for complete search history.

(56) References Cited

U.S. PATENT DOCUMENTS

| 6,911,443 | B2 | 6/2005 | Yura et al. | |
|---|---|---|---|---|
| 8,293,923 | B2 | 10/2012 | Guckian et al. | |
| 2011/0152273 | A1* | 6/2011 | Arikawa | A61P 21/00 514/249 |
| 2013/0274241 | A1 | 10/2013 | Jorand-Lebrun et al. | |
| 2020/0216413 | A1 | 7/2020 | Beddies et al. | |

FOREIGN PATENT DOCUMENTS

| EP | 1184376 A1 | 3/2002 | |
|---|---|---|---|
| WO | 2001/09134 A1 | 2/2001 | |
| WO | 2001/83485 A1 | 11/2001 | |
| WO | 2003/057695 A1 | 7/2003 | |
| WO | 2003/063794 A1 | 8/2003 | |
| WO | 2004/087699 A2 | 10/2004 | |
| WO | 2005/012294 A1 | 2/2005 | |
| WO | 2006/129100 A1 | 12/2006 | |
| WO | 2008/079907 A1 | 7/2008 | |
| WO | 2008/109943 A1 | 9/2008 | |
| WO | 2009/026107 A1 | 2/2009 | |
| WO | 2009/136995 A2 | 11/2009 | |
| WO | 2009/145856 A1 | 12/2009 | |
| WO | 2010/068257 A1 | 6/2010 | |
| WO | 2011/075515 A1 | 6/2011 | |
| WO | 2011/079051 A1 | 6/2011 | |
| WO | 2012/123311 A1 | 9/2012 | |
| WO | 2012/177714 A1 | 12/2012 | |
| WO | WO2012177714 | * 12/2012 | ........... C07D 471/04 |
| WO | 2015/100217 A1 | 7/2015 | |
| WO | 2015/131080 A1 | 9/2015 | |
| WO | 2016/097862 A2 | 6/2016 | |
| WO | 2016/138352 A1 | 9/2016 | |
| WO | 2017/207481 A1 | 12/2017 | |

OTHER PUBLICATIONS

Lam et al., (2016) BioOrg. & Med. Chem. Let. vol. 26 (24), pp. 5947-5950.*
Vippagunta et al (2001).*
Ahmad, et al., "Increased expression of the interleukin-1 receptor-associated kinase (IRAK)-1 is associated with adipose tissue inflammatory state in obesity," Diabetology & Metabolic Syndrome, (2015), vol. 7: 71-.
Hynes, Jr., et al., "Chapter Nine—Advances in the Discovery of Small-Molecule IRAK4 Inhibitors," Annual Reports in Medicinal Chemistry, (2014), vol. 49: 117-133. Abstract only.
Bajpai, et al., "Spleen tyrosine kinase: a novel target for therapeutic intervention of rheumatoid arthritis," Expert Opin. Investig. Drugs, (2008), vol. 17, No. 5: 641-659.
European Search Report & Written Opinion of EP17197344.9, dated Dec. 19, 2017.
International Preliminary Search Report & Written Opinion of PCT/EP2018/078086, dated Apr. 21, 2020.
International Search Report & Written Opinion of PCT/EP2018/078086, dated Nov. 8, 2018.
Cameron, et al., "Loss of Interleukin Receptor-Associated Kinase 4 Signaling Suppresses Amyloid Pathology and Alters Microglial Phenotype in a Mouse Model of Alzheimer's Disease," The Journal of Neuroscience, (2012), vol. 32, No. 43: 15112-15123.

(Continued)

*Primary Examiner* — Paul V Ward
(74) *Attorney, Agent, or Firm* — McBee Moore & Vanik IP, LLC

(57) ABSTRACT

The present application relates to the use of fused heteroaromatic pyrrolidones for treatment and/or prophylaxis of allergic and/or inflammatory diseases in animals and to the use thereof for production of medicaments for treatment and/or prophylaxis of allergic and/or inflammatory diseases in animals, especially of atopic dermatitis and/or Flea Allergy Dermatitis, and especially in domestic animals, particularly in dogs.

15 Claims, 2 Drawing Sheets

(56) References Cited

OTHER PUBLICATIONS

Chesney, C.J., "Species of flea found on cats and dogs in south west England: further evidence of their polyxenous state and implications for flea control," Veterinary Record, (1995), vol. 136, No. 14: 356-358. Abstract only.

Bossaller, et al., "Cutting Edge: FAS (CD95) Mediates Noncanonical IL-1b and IL-18 Maturation via Caspase-8 in an RIP3-Independent Manner," The Journal of Immunology, (2012), vol. 189: 5508-5512.

Datta, et al., "Toll IL-1 Receptors Differ in Their Ability to Promote the Stabilization of Adenosine and Uridine-Rich Elements Containing mRNA1," The Journal of Immunology, (2004), vol. 173: 2755-2761.

Denyer, et al., "Syk Kinase Inhibitors in Allergic Diseases," Drug News Perspective, (2009), vol. 22, No. 3: 146-150.

Dinarello, C.A., "Immunological and Inflammatory Functions of the Interleukin-1 Family," Annu. Rev. Immunol., (2009), vol. 27: 519-550.

Flannery, et al., "The interleukin-1 receptor-associated kinases: critical regulators of innate immune signalling," Biochemical Pharmacology, (2008).

Halliwell, R. "Revised nomenclature for veterinary allergy," Veterinary Immunology and Immunopathology, (2006), vol. 114: 207-208.

Holtmann, et al., "The MAPK Kinase Kinase TAK1 Plays a Central Role in Coupling the Interleukin-1 Receptor to Both Transcriptional and RNA-targeted Mechanisms of Gene Regulation*," Journal of Biological Chemistry, (2001), vol. 276, No. 5: 3508-3516.

Janeway, et al., "Innate Immune Recognition," Annu. Rev. Immunol., (2002), vol. 20: 197-216.

Kim, et al., "The Critical Role of IL-1Receptor-Associated Kinase 4-Mediated NF-kB Activation in Modified Low-Density Lipoprotein-Induced Inflammatory Gene Expression and Atherosclerosis," The Journal of Immunology, (2011), vol. 186:2871-2880.

Kollewe, et al., "Sequential Autophosphorylation Steps in the Interleukin-1 Receptor-associated Kinase-1 Regulate its Availability as an Adapter in Interleukin-1 Signaling," Journal of Biological Chemistry, (2004), vol. 279, No. 7: 5227-5236.

Lam, et al., "Discovery of TAK-659 an orally available investigational inhibitor of Spleen Tyrosine Kinase (SYK)," Bioorganic & Medicinal Chemistry Letters, (2016), vol. 26, No. 24: 5947-5950.

Maekawa, et al., "Survival and Cardiac Remodeling After Myocardial Infarction Are Critically Dependent on the Host Innate Immune Interleukin-1 Receptor-Associated Kinase-4 Signaling," Circulation, (2009), vol. 120, Issue 14: 1401-1414.

Masuda, et al., "Syk inhibitors as treatment for allergic rhinitis," Pulmonary Pharmacology & Therapeutics, (2008), vol. 21: 461-467.

Mcgettrick, et al., "Toll-like receptors: key activators of leucocytes and regulator of haematopoiesis," British Journal of Haematology, (2007), vol. 139: 185-193.

Nuttall, et al., "Canine atopic dermatitis—what have we learned?" Vet. Record, (2013), 201-207.

Podolanczuk, et al., "Of mice and men: an open-label pilot study for treatment of immune thrombocytopenic purpura by an inhibitor of Syk," Blood, (2009), vol. 113, No. 14: 3154-3160.

Motshwene, et al., "An Oligomeric Signaling Platform Formed by the Toll-like Receptor Signal Transducers MyD88 and IRAK-4," J. Biol. Chem., (2009), vol. 284, No. 37: 25404-25411.

Rekhter, et al., "Genetic ablation of IRAK4 kinase activity inhibits vascular lesion formation," Biochemical and Biophysical Research Communication, (2008), vol. 367: 642-648.

Staschke, et al., "IRAK4 Kinase Activity Is Required for Th17 Differentiationand Th17-Mediated Disease," The Journal of Immunology, (2009), pp. 568-577.

Wan, et al., "The kinase TAK1 integrates antigen and cytokine receptor signaling for T cell development, survival and function," Nat Immunol, (2006), vol. 7, No. 8: 851-858.

Wong, et al., "Targeting Syk as a treatment for allergic and autoimmune disorders," Expert Opin. Investig. Drugs, (2004), vol. 13, No. 7: 743-762.

* cited by examiner

USE OF FUSED HETEROAROMATIC PYRROLIDONES FOR TREATMENT AND PREVENTION OF DISEASES IN ANIMALS

CROSS REFERENCE TO RELATED APPLICATIONS

This application is a § 371 National State Application of PCT/EP2018/078086, filed Oct. 15, 2018, which claims priority to European Application No. 17197344.9 filed Oct. 19, 2017.

The present application relates to the use of fused heteroaromatic pyrrolidones for treatment and/or prophylaxis of inflammatory and/or allergic diseases in animals and to the use thereof for production of medicaments for treatment and/or prophylaxis of inflammatory and/or allergic diseases in animals, especially of Atopic Dermatitis and/or Flea Allergy Dermatitis (FAD), and especially in domestic animals, particularly in dogs and cats.

The present invention relates to the use of fused heteroaromatic pyrrolidones of the general formula (I) in animals, which inhibit the spleen tyrosine kinase (Syk), the interleukin-1 receptor-associated kinase 4 (IRAK4) and/or the Janus kinase (JAK).

BACKGROUND

Spleen tyrosine kinase (SYK) is a 72 kDa non-receptor cytoplasmic tyrosine kinase that is essential in the transmission of activating signals from the B-cell receptor (BCR). SYK has a primary amino acid sequence similar to that of zeta-associated protein-70 (ZAP-70) and is involved in receptor-mediated signal transduction. The N-terminal domain of SYK contains two Src-homology 2 (SH2) domains, which bind to diphosphorylated immunoreceptor tyrosine-based activation motifs (ITAMs) that can be found in the cytoplasmic signaling domains of many immunoreceptor complexes. The C-terminus contains the catalytic domain, and includes several catalytic loop autophosphorylation sites that are responsible for receptor-induced SYK activation and subsequent downstream signal propagation. SYK is expressed in many cell types involved in adaptive and innate immunity, including lymphocytes (B cells, T cells, and NK cells), granulocytes (basophils, neutrophils, and eosinophils), monocytes, macrophages, dendritic cells, and mast cells. Syk is primarily expressed in haematopoietic cells and appears to be particularly important in B cells. SYK's role in ITAM-dependent signaling and its expression in many cell types suggest that compounds which inhibit SYK activity may be useful for treating disorders involving the immune system and inflammation. Such disorders include Type I hypersensitivity reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); and inflammation of the lung (chronic obstructive pulmonary disease). See e.g., Brian R. Wong et al., Expert Opin. Investig. Drugs (2004) 13(7):743-62; Sanderson et al. (2009); Jane Denyer & Vipul Patel, Drug News Perspective (2009) 22(3): 146-50; Esteban S. Masuda & Jochen Schmitz, Pulmonary Pharmacology & Therapeutics (2008) 21:461-67; Malini Bajpai et al., Expert Opin. Investig. Drugs (2008) 17(5):641-59; and Anna Podolanczuk et al., Blood (2009) 113:3 1 54-60. Inhibitors of Syk are potentially useful in treating asthma, leukaemia and lymphomas.

Various SYK inhibitors have been described in Expert Opin. Ther. Patents (2014) 24(5):573-595, providing a review of the published patent applications relating to SYK inhibitors. Examples of patent applications relating to SYK inhibitors comprise, e.g., EP 1184376 A1, WO01/83485 A1, WO 03/057695 A1, WO2006/129100 A1, WO01/09134 A1, WO03/063794 A1, WO2005/012294 A1, WO2004/087699 A2, WO2009/026107 A1, WO2009136995 A2, WO2009/145856 A1, WO2010/068257 A1, WO2015/100217 A1, WO2011/075515 A1, WO2012/123311 A1, WO2011/079051 A1 and WO2016/097862 A2.

Therefrom, in particular WO2011/079051 A1 and WO2016/097862 A2 describe fused heteroaromatic pyrrolidones as defined in the formula (I) of the present invention and their activity as SYK inhibitor for treating disorders or conditions associated with SYK inhibition in humans. More particularly, WO2011/079051 A1 and WO2016/097862 A2 both focus on the treatment of disorders and conditions involving the immune system and inflammation, including rheumatoid arthritis, in humans as well as on the treatment of diseases or conditions selected from a hematological malignancy and an epithelial cancer. One specific example compound of WO2011/079051 A1 is 6-((1R,2S)-2-aminocyclohexylamino)-7-fluoro-4-(1-methyl-1H-pyrazol-4-yl)-1H-pyrrolo[3,4-c]pyridine-3(2H)-one (Example Compound 28) having the formula

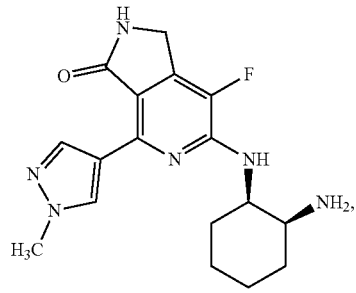 [SMILES: Cn1cc(-c2nc(N[C@@H]3CCCC[C@@H]3N)c(F)c3c2C(=O)NC3)cn1]

which is also the object of WO2016/097862 A2 (Compound I). Said compound is under clinical evaluation in a phase II study with respect to its anti-tumor activity, in particular for its activity against advanced solid tumor and lymphoma malignancies such as chronic lymphocytic leukemia (CLL), peripheral T-cell lymphoma (PTCL), acute myeloid leukemia (AML) and diffuse large B-cell lymphoma (DLBCL) in humans (B. Lam et al.; Bioorganic Medicinal Chemistry Letters, 26 (2016); J. Yu et al. Journal of Clinical Oncology 34, no. 15 Suppl. (2016)).

Another example compound of WO2011/079051 A1 is 6-((1R,2S)-2-aminocyclohexylamino)-7-chloro-4-(1-methyl-1H-pyrazol-4-yl)-1H-pyrrolo[3,4-c]pyridine-3(2H)-one (Example Compound 29) having the formula

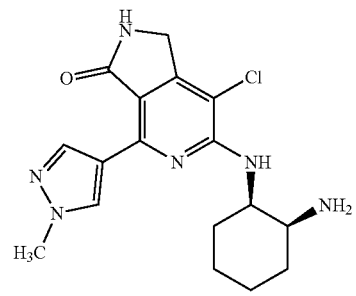 [SMILES: Cn1cc(-c2nc(N[C@@H]3CCCC[C@@H]3N)c(Cl)c3c2C(=O)NC3)cn1]

IRAK4 (interleukin-1 receptor-associated kinase 4) plays a key role in the activation of the immune system. Therefore, this kinase is an important therapeutic target molecule for the development of inflammation-inhibiting substances. IRAK4 is expressed by a multitude of cells and mediates the signal transduction of Toll-like receptors (TLRs), except TLR3, and receptors of the interleukin (IL)-1β family consisting of the IL-1R (receptor), IL-18R, IL-33R and IL-36R (Janeway and Medzhitov, Annu. Rev. Immunol., 2002; Dinarello, Annu. Rev. Immunol., 2009; Flannery and Bowie, Biochemical Pharmacology, 2010). The binding of the TLR ligands or the ligands of the IL-13 family to the respective receptor leads to recruitment and binding of MyD88 [Myeloid differentiation primary response gene (88)] to the receptor. As a result, MyD88 interacts with IRAK4, resulting in the formation of an active complex which interacts with and activates the kinases IRAK1 or IRAK2 (Kollewe, Mackensen, et al., Journal of Biological Chemistry, 2004; Precious et al., J. Biol. Chem., 2009). As a result of this, the NF (nuclear factor)-κB signalling pathway and the MAPK (mitogen-activated protein kinase) signal pathway are activated (Wang, Deng, et al., Nature, 2001). The activation both of the NF-κB signal pathway and of the MAPK signal pathway leads to processes associated with different immune processes. For example, there is increased expression of various inflammatory signal molecules and enzymes such as cytokines, chemokines and COX-2 (cyclooxygenase-2), and increased mRNA stability of inflammation-associated genes, for example COX-2, IL-6 (interleukin-6), IL-8 (Holtmann, Enninga, et al., Journal of Biological Chemistry, 2001; Datta, Novotny, et al., The Journal of Immunology, 2004). Furthermore, these processes may be associated with the proliferation and differentiation of particular cell types, for example monocytes, macrophages, dendritic cells, T cells and B cells (Wan, Chi, et al., Nat Immunol, 2006; McGettrick and J. O'Neill, British Journal of Haematology, 2007). The central role of IRAK4 in the pathology of various inflammatory disorders had already been shown by direct comparison of wild-type (WT) mice with genetically modified animals having a kinase-inactivated form of IRAK4 (IRAK4 KDKI). IRAK4 KDKI animals have an improved clinical picture in the animal model of multiple sclerosis, atherosclerosis, myocardial infarction and Alzheimer's disease (Rekhter, Staschke, et al., Biochemical and Biophysical Research Communication, 2008; Maekawa, Mizue, et al., Circulation, 2009; Staschke, Dong, et al., The Journal of Immunology, 2009; Kim, Febbraio, et al., The Journal of Immunology, 2011; Cameron, Tse, et al., The Journal of Neuroscience, 2012). In addition, the high relevance of IRAK4 for immune complex-mediated IFNα (interferon-alpha) production by plasmacytoid dendritic cells, a key process in the pathogenesis of systemic lupus erythematosus (SLE), has been shown (Chiang et al., The Journal of Immunology, 2010). Furthermore, the signalling pathway is associated with obesity (Ahmad, R., P. Shihab, et al., Diabetology & Metabolic Syndrome, 2015). As well as the essential role of IRAK4 in congenital immunity, there are also hints that IRAK4 influences the differentiation of Th17 T cells, components of adaptive immunity. In the absence of IRAK4 kinase activity, fewer IL-17-producing T cells (Th17 T cells) are generated compared to WT mice.

The prior art discloses a multitude of IRAK4 inhibitors (see, for example, Annual Reports in Medicinal Chemistry (2014), 49, 117-133). U.S. Pat. No. 8,293,923 and US20130274241 disclose IRAK4 inhibitors having a 3-substituted indazole structure. The to date unpublished application PCT/EP2017/062876 describes the activity of substituted indazoles as IRAK4 inhibitors and the use thereof for the treatment and prevention of diseases in animals, in particular Canine Atopic Dermatitis (CAD) and FAD.

Janus kinase (JAK) is another of ten recognized families of non-receptor tyrosine kinases. It transduces cytokine-mediated signals via the JAK-STAT pathway. In the JAK pathway cytokines bind to a unique cellmembrane receptor and trigger the specific intracellular JAK pathway, which drives itch and inflammation in the skin. Cytokines implicated in allergic skin disease, such as IL-31, IL-13 and IL-4 bind to their receptor on the cell membrane and activate the JAK pathway. JAKs induce gene transcription and biological responses. For example, IL-31 can activate sensory neurons to induce pruritus. The JAKs possess two near-identical phosphate-transferring domains. One domain exhibits the kinase activity, while the other negatively regulates the kinase activity of the first. JAKs are kinases which phosphorylate a group of proteins called Signal Transduction and Activators of Transcription or STATs. When phosphorylated, STATs dimerize, translocate to the nucleus and activate expression of genes which lead to, amongst other things, cellular proliferation. The central role played by the JAK family of protein tyrosine kinases in the cytokine dependent regulation of both proliferation and end function of several important cell types indicates that agents capable of inhibiting the JAK kinases are useful in the prevention and chemotherapeutic treatment of disease states dependent on these enzymes.

Mammals have four members of this family, JAK1, JAK2, JAK3 and Tyrosine kinase 2 (TYK2). Potent and specific inhibitors of each of the currently known four JAK family members are expected to provide a means of inhibiting the action of the cytokines that drive immunological and inflammatory diseases. JAK inhibitors are thus under development for the treatment of psoriasis, rheumatoid arthritis, polycythemia vera, alopecia, essential thrombocythemia, ulcerative colitis, myeloid metaplasia with myelofibrosis and vitiligo. Examples of JAK inhibitors are described e.g. in WO2008/109943 A1. The term "JAK" or "JAKs" as used herein shall include all and any combination of one or more of JAK1, JAK2, JAK3 and TYK2, unless explicitly stated otherwise.

It has also been described that some compounds act as dual SYK/JAK inhibitors, which are considered as potentially useful in treating inflammatory diseases. It is speculated that dual SYK/JAK inhibitors might offer better therapeutic efficacy but data have not yet to been reported to validate such a hypothesis. Examples referring to compounds having dual activity both as SYK and JAK inhibitor have been described e.g. in WO2008/079907 A1, WO2009/136995 A2 and WO2009/145856 A1.

SYK, JAKs and IRAK4, are all involved in the signalling of allergic processes which play an important role in the pathogenesis of allergic skin diseases, like CAD.

CAD is increasingly considered a clinical syndrome with a variety of manifestations and potential underlying causes that vary from patient to patient (DeBoer, Veterinary Allergy, 2014). One of the reasons for this complexity is the underlying biphasic immune response where a Th2 response predominates in the acute phase (including cytokines as IL-4, IL-5, IL-13) and a Th1 response with a different cytokine profile predominating in the chronic phase (Marsella, Veterinary Allergy, 2014). In addition to this, the pathophysiology of skin inflammation and pruritus, even when intercorrelated, seem to depend on different immune and neurological pathways. Allergic inflammatory diseases such as CAD are commonly diagnosed by veterinarians.

Current treatment options for allergic and/or inflammatory diseases in animals, for example for allergic skin diseases, typically include the use of steroids and cyclosporine—both are associated with side effects.

Recently a JAK-inhibitor has been approved for use in CAD that clinically provides relief from pruritus; however, the dosing regimen may again be limited by side effects. Therefore, the treatment of CAD with a disease modifying agent that is able to delay disease progression while at the same time substantially reducing pruritus without treatment-related side effects would allow long-term treatment which to date remains an unmet medical need.

CAD is one of the most common diseases of dogs. CAD can affect patients from an early age, recurring throughout their lifetime and is the second most common cause of canine pruritus after FAD. CAD can be defined as a 'genetically predisposed inflammatory and pruritic allergic skin disease with characteristic clinical features associated with IgE, most commonly directed against environmental allergens' (Halliwell, Veterinary Immunology and Immunopathology, 2006), like dust mites and pollen, which are incredibly difficult for pets to avoid, since dust mites are virtually everywhere and pollen permeates the air outdoors. CAD is a complex and multifactorial disease involving immune dysregulation, allergic sensitisation, skin barrier defects, microbial colonization and environmental factors. IgE is not a prerequisite for the development of the clinical signs in all cases, and a separate clinical entity known as atopic-like dermatitis was defined as 'an inflammatory and pruritic skin disease with clinical features identical to those seen in Canine Atopic Dermatitis in which an IgE response to environmental or other allergens cannot be documented' (Nuttall et al., Vet. Record, 2013). The most common clinical signs of CAD include itching, excessive scratching, rubbing on the carpet, hair loss (alopecia), greasy or flaky skin with a foul odor, excessive chewing on the paws and areas such as the groin and armpits. Over time, the skin that is scratched can develop hot spots—raw, inflamed areas—that may become infected.

At present, the treatment of acute flares of Atopic Dermatitis involves the search for, and then elimination of, the cause of the flares, bathing with mild shampoos, and controlling pruritus and skin lesions with interventions that include topical and/or oral glucocorticoids or oclacitinib. For chronic CAD, the first steps in management are the identification and avoidance of flare factors, as well as ensuring that there is adequate skin and coat hygiene and care; this might include more frequent bathing and possibly increasing essential fatty acid intake. The medications currently most effective in reducing chronic pruritus and skin lesions are topical and oral glucocorticoids, oral ciclosporin, oral oclacitinib, and, where available, injectable recombinant interferons. Allergen-specific immunotherapy (ASIT) and proactive intermittent topical glucocorticoid applications are the only interventions likely to prevent or delay the recurrence of flares of Atopic Dermatitis (Olivry et al., BMC Veterinary Research, 2015)

FAD, or flea bite hypersensitivity, is the most common dermatologic disease of domestic dogs (Scott et al., In: Muller and Kirk's Small Animal Dermatology, 2001), caused by the by far most prevalent flea on dogs and cats: *Ctenocephalides felis* (Beresford-Jones, J Small Animal Practice, 1981; Chesney, Veterinary Record, 1995). Cats also develop FAD, which is one of the major causes of feline miliary dermatitis. FAD is most prevalent in the summer, although in warm climates flea infestations may persist throughout the year. In north temperate regions, the close association of pets and their fleas with human dwellings creates conditions that permit a year-round problem. Temperature extremes and low humidity tend to inhibit flea development. When feeding, fleas inject saliva that contains a variety of histamine-like compounds, enzymes, polypeptides, and amino acids that span a wide range of sizes (40-60 kD) and induce Type I, Type IV, and basophil hypersensitivity. Flea-naïve dogs exposed intermittently to flea bites develop either immediate (15 min) or delayed (24-48 hr) reactions, or both, and detectable levels of both circulating IgE and IgG antiflea antibodies. Dogs exposed continuously to flea bites have low levels of these circulating antibodies and either do not develop skin reactions or develop them later and to a considerably reduced degree. This could indicate that immunologic tolerance may develop naturally in dogs continually exposed to flea bites. Although the pathophysiology of FAD in cats is poorly understood, similar mechanisms may exist.

The cat flea (*Ctencephalides felis*) causes severe irritation in animals and people, and is responsible for FAD. Typical clinical signs are: pruritus, inflammation of the skin and skin lesions (erythema, scales, papules, crusts and lichenification). These lesions are most commonly seen along the back and at the base of the tail. As the condition progresses there may be hair loss, broken hairs, oozing or crusty sores, pimply bumps and general redness and inflammation of the skin. The sores can be very painful. In severe cases the skin becomes thickened and dark, predominantly in the area on the dog's back at the base of the tail. The dog, itself, causes the damage with self mutilation due to the severe itching. In general, prevention and treatment of flea infestation is the treatment option of choice. Most commonly neonicotinoids, like imidacloprid, or gamma-aminobutyric acid (GABA)-gated chloride channel blockers, like fipronil, are used. In cases where symptoms of skin allergic dermatitis do not resolve, current treatments mentioned under CAD, like topical and oral glucocorticoids, oral ciclosporin, oral oclacitinib are used.

SUMMARY

Cytokines can trigger and perpetuate the clinical signs of itching, scratching and inflammation. Pruritogenic and proinflammatory cytokines in skin diseases are IL-2, IL-4, IL-6, IL-13, IL-18, IL-31, IL-33. To date the standard kinase inhibitors are only able to reduce pruritus fast, whereas the reduction of skin inflammation is delayed for up to one week mainly due to their mode of action.

The problem addressed by the present invention was therefore providing a more comprehensive treatment option covering different immune and neurological pathways for inflammatory and/or allergic diseases in animals that single signaling pathways may not cover for. In a further aspect the problem addressed by the present invention is that of providing a more comprehensive treatment option for CAD and/or FAD, and especially in domestic animals, particularly in dogs. A further problem addressed by the present invention was the delayed mode of action for reduction of skin inflammation of the standard kinase inhibitors.

It has now been surprisingly found that the compounds of present invention act as inhibitors of at least one of SYK, JAK and/or IRAK4 in animals and therefore have an unexpected and very comprehensive and fast pharmacological activity spectrum in the treatment and/or prophylaxis of allergic and/or inflammatory diseases in animals. A further aspect of the present invention relates to the dual activity of the compounds as described herein as SYK and JAK (SYK/

JAK), SYK and IRAK 4 (SYK/IRAK4) or JAK and IRAK4 (JAK/IRAK4) inhibitor. A further aspect of the present invention relates to the triple activity of the compounds as described herein as SYK and JAK and IRAK 4 (SYK/JAK/IRAK4) inhibitor. Therein, in each case "JAK" relates to all or any combination of one or more of the JAK family, i.e. JAK1, JAK2, JAK3 and TYK2, unless explicitly stated otherwise.

DETAILED DESCRIPTION OF THE INVENTION

Figure 1:
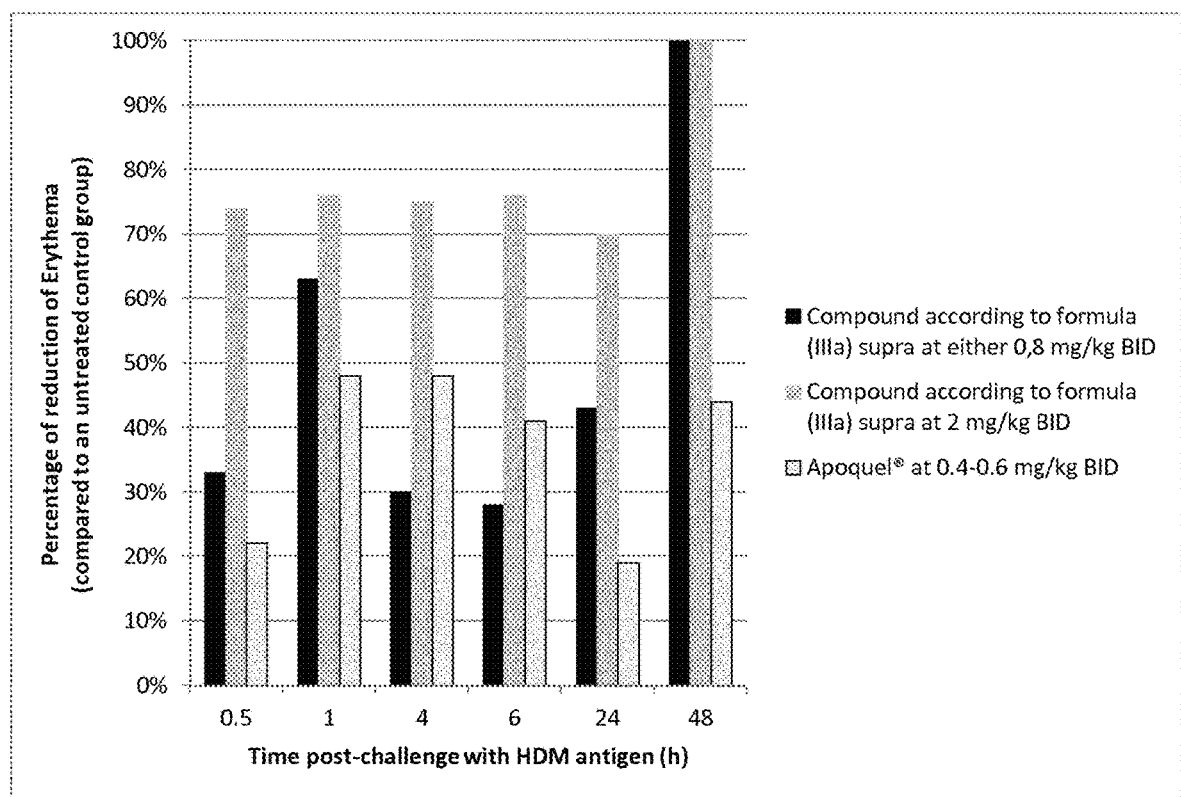
FIG. 1 shows a comparative reduction of erythema in the CAD model (expressed as % compared the control group) after treatment of up to >75% when administered at 2 mg/kg BID with a compound of formula (IIIa)

The inhibitors are especially suitable for treatment and for prevention of inflammatory disorders in animals characterized by an overreacting immune system. Particular mention should be made here of Atopic Dermatitis, FAD in dogs and cats, inflammatory bowel disease in dogs and cats, osteoarthritis and inflammatory pain in dogs, cats, horses and cattle, non-infectious recurrent airway disease in horses (also known as chronic obstructive pulmonary disease, heaves), insect hypersensitivity in horses (also known as sweet itch, summer eczema), feline asthma, bovine respiratory disease, mastitis and endometritis in cattle, and swine respiratory disease. Atopic dermatitis, for example, is a common disease in companion animals, particularly in cats and dogs.

In a first aspect, the present invention provides compounds of the general formula (I)

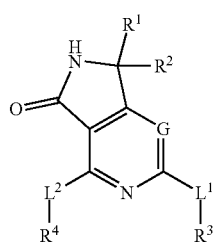

(I)

in which:
G is selected from N and $C(R^5)$;
$L^1$ and $L^2$ are each independently selected from —NH— and a bond; $R^1$ and $R^2$ are each independently selected from hydrogen, halogen, $C_{1-3}$-alkyl, and $C_{1-3}$-halogenoalkyl having 1 to 5 halogen atoms, or $R^1$ and $R^2$, together with the atom to which they are attached, form a $C_{3-6}$-cycloalkyl;

$R^3$ is selected from $C_{2-6}$-alkyl, $C_{3-8}$-cycloalkyl, $C_{2-5}$-heterocyclyl, and $C_{1-9}$-heteroaryl, each optionally substituted with one to five substituents independently selected from halogen, oxo, —NO$_2$, —CN, $R^6$ and $R^7$;

$R^4$ is selected from $C_{3-8}$-cycloalkyl, $C_{2-5}$-heterocyclyl, $C_{6-14}$-aryl and $C_{1-9}$-heteroaryl, each optionally substituted with one to five substituents independently selected from halogen, oxo, —CN, $R^6$ and $R^7$;

$R^5$ is selected from hydrogen, halogen, —CN, $C_{1-4}$-alkyl, $C_{2-4}$-alkenyl, $C_{2-4}$-alkynyl, $C_{2-5}$-heterocyclyl, $C_{1-8}$-heteroaryl, and $R^{10}$, wherein the alkyl, alkenyl, alkynyl moieties are each optionally substituted with one to five substituents independently selected from halogen, —CN, oxo, and $R^{10}$, and wherein the heterocyclyl moiety has 3 to 6 ring atoms and the heteroaryl moiety has 5 or 6 ring atoms, and the heterocyclyl and heteroaryl moieties are each optionally substituted with one to four substituents independently selected from halogen, —NO$_2$, —CN, $C_{1-4}$-alkyl,
$C_{2-4}$-alkenyl, $C_{2-4}$-alkynyl, $C_{1-4}$-halogenoalkyl having 1 to 5 halogen atoms, and $R^{10}$;

each $R^6$ is independently selected from —OR$^8$, —N(R$^8$)R$^9$, —NR$^8$C(O)R$^9$, —C(O)R$^8$, —C(O)OR$^8$, —C(O)N(R$^8$)R$^9$, —C(O)N(R$^8$)OR$^9$, —C(O)N(R$^8$)S(O)$_2$R$^9$, —N(R$^8$)S(O)$_2$R$^9$, —S(O)$_n$R$^8$, and —S(O)$_2$N(R$^8$)R$^9$;

each $R^7$ is independently selected from $C_{1-6}$-alkyl, $C_{2-6}$-alkenyl, $C_{2-6}$-alkynyl, $C_{3-6}$-cycloalkyl-(CH$_2$)$_m$—, $C_{6-14}$-aryl-(CH$_2$)$_m$—, $C_{2-5}$-heterocyclyl-(CH$_2$)$_m$—, and $C_{1-9}$-heteroaryl-(CH$_2$)$_m$—, each optionally substituted with one to five substituents independently selected from halogen, oxo, —NO$_2$, —CN, $C_{1-6}$-alkyl, $C_{1-6}$-halogenoalkyl having 1 to 5 halogen atoms, and $R^{10}$;

each $R^8$ and $R^9$ is independently selected from hydrogen or from $C_{1-6}$-alkyl, $C_{2-6}$-alkenyl, $C_{2-6}$-alkynyl, $C_{3-6}$-cycloalkyl-(CH$_2$)$_m$—, $C_{6-14}$-aryl-(CH$_2$)$_m$—, $C_{2-5}$-heterocyclyl-(CH$_2$)$_m$— and $C_{1-9}$-heteroaryl-(CH$_2$)$_m$—, each optionally substituted with one to five substituents independently selected from halogen, oxo, —NO$_2$, —CN, $C_{1-6}$-alkyl, $C_{1-6}$-halogenoalkyl having 1 to 5 halogen atoms, and $R^{10}$;

each $R^{10}$ is independently selected from —OR$^{11}$, —N(R$^{11}$)R$^{12}$, —N(R$^{11}$)C(O)R$^{12}$, —C(O)R$^{11}$, —C(O)OR$^{11}$, —C(O)N(R$^{11}$)R$^{12}$, —C(O)N(R$^{11}$)OR$^{12}$, —C(O)N(R$^{11}$)S(O)$_2$R$^{12}$, —NR$^{11}$S(O)$_2$R$^{12}$, —S(O)$_n$R$^{11}$, and —S(O)$_2$N(R$^{11}$)R$^{12}$;

each $R^{11}$ and $R^{12}$ is independently selected from hydrogen and $C_{1-6}$-alkyl;

each n is independently selected from 0, 1 and 2; and
each m is independently selected from 0, 1, 2, 3, and 4;
wherein each of the aforementioned heteroaryl moieties has one to four heteroatoms independently selected from N, O, and S, and each of the aforementioned heterocyclyl moieties is saturated or partially unsaturated and has one or two heteroatoms independently selected from N, O, and S;

and the diastereomers, enantiomers, metabolites, salts, solvates or solvates of the salts thereof, for use in the treatment and/or prophylaxis of allergic and/or inflammatory diseases in animals.

In the case of the mentioned use of the compounds according to formula (I) as described herein and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if compounds according to formula (I) as described herein or working examples or salts thereof were obtained in the form of solvates, for example hydrates, of unknown stoichiometric composition (if they are of a defined type) by the preparation and/or purification processes described.

Present compounds are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by the formula (I) and are mentioned below as embodiments and the salts, solvates and solvates of the salts thereof if the compounds that are encompassed by the formula (I) and are mentioned below are not already salts, solvates and solvates of the salts.

Preferred salts in the context of the present invention are physiologically acceptable salts of the present compounds. However, the present disclosure also encompasses salts which themselves are unsuitable for pharmaceutical applications but which can be used, for example, for the isolation or purification of the present compounds.

Physiologically acceptable salts of the present compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the present compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the present compounds which form a complex in the solid or liquid state by coordination with solvent molecules. Hydrates are a specific form of the solvates in which the coordination is with water.

The present compounds may, depending on their structure, exist in different stereoisomeric forms, i.e. in the form of configurational isomers or else, if appropriate, of conformational isomers (enantiomers and/or diastereomers, including those in the case of atropisomers). The present invention therefore encompasses the use of enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

If the present compounds can occur in tautomeric forms, the present invention encompasses the use of all the tautomeric forms.

The present invention also encompasses the use of all suitable isotopic variants of the present compounds. An isotopic variant of an present compound is understood here as meaning a compound in which at least one atom within the present compound has been exchanged for another atom of the same atomic number, but with a different atomic mass than the atomic mass which usually or predominantly occurs in nature. Examples of isotopes which can be incorporated into an present compound are those of hydrogen, carbon, nitrogen, oxygen, phosphorus, sulphur, fluorine, chlorine, bromine and iodine, such as 2H (deuterium), 3H (tritium), 13C, 14C, 15N, 17O, 18O, 32P, 33P, 33S, 34S, 35S, 36S, 18F, 36Cl, 82Br, 123I, 124I, 129I and 131I. Particular isotopic variants of an present compound, such as, in particular, those in which one or more radioactive isotopes have been incorporated, may be beneficial, for example, for the examination of the mechanism of action or of the active ingredient distribution in the body; because of the comparative ease of preparability and detectability, particularly compounds labelled with 3H or 14C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the present compounds may therefore in some cases also constitute a preferred embodiment of the use of the present invention. Isotopic variants of the present compounds can be prepared by the processes known to those skilled in the art, for example by the methods described further below and the procedures described in the working examples, by using corresponding isotopic modifications of the respective reagents and/or starting compounds.

The present invention further provides the use of all the possible crystalline and polymorphous forms of the present compounds, where the polymorphs may be present either as single polymorphs or as a mixture of a plurality of polymorphs in all concentration ranges.

The present invention additionally also encompasses the use of prodrugs of the present compounds. The term "prodrugs" in this context refers to compounds which may themselves be biologically active or inactive but are converted (for example metabolically or hydrolytically) to present compounds during their residence time in the body.

In the context of the present invention, unless specified otherwise, the substituents have the following meanings:

"Alkyl" in the context of the invention represents a straight-chain or branched alkyl group having the particular number of carbon atoms specified (e.g., $C_{1-3}$-alkyl refers to an alkyl group having 1 to 3 carbon atoms, $C_{1-6}$-alkyl refers to an alkyl group having 1 to 6 carbon atoms, and so on). Examples include methyl, ethyl, n-propyl, isopropyl, n-butyl, isobutyl, 1-methylpropyl, 2-methylpropyl, tert-butyl, n-pentyl, 1-ethylpropyl, 1-methylbutyl, 2-methylbutyl, 3-methylbutyl, 2,2-dimethylpropyl, n-hexyl, 1-methylpentyl, 2-methylpentyl, 3-methylpentyl, 4-methylpentyl, 1-ethylbutyl and 2-ethylbutyl. Preference is given to methyl, ethyl, n-propyl, n-butyl, 2-methylbutyl, 3-methylbutyl and 2,2-dimethylpropyl.

"Alk-1-yl" refers to an alkyl group, as defined above, which is attached to a parent group or substrate through a carbon atom located at the 1 position of the alkyl group.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms.

Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Cycloalkyl" in the context of the invention is a monocyclic or bicyclic saturated alkyl group having the number of carbon atoms specified in each case (e.g. $C_{3-8}$-cycloalkyl refers to a cycloalkyl group having 3 to 8 carbon atoms as ring members). Preferred examples of monocyclic cycloalkyl include cyclopropyl, cyclobutyl, cyclopentyl and cyclohexyl. Bicyclic saturated alkyl groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached to a parent group or to a substrate at any ring atom unless such attachment would violate valence requirements. In addition, the cycloalkyl group may include one or more non-hydrogen substituents unless such substitution would violate valence requirements. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalk-1-yl" refers to a cycloalkyl group, as defined above, which is attached to a parent group or substrate through a carbon atom located at the 1 position of the cycloalkyl group.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached to a parent group or to a substrate at any ring atom and may include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$-aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen (N), oxygen (O), and sulfur (S). Both the monocyclic and bicyclic groups generally have a specified number of carbon atoms in their ring or rings (e.g., $C_{2-5}$-heterocyclyl refers to a heterocyclyl group having 2 to 5 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached to a parent group or to a substrate at any ring atom and may include one or more non-hydrogen substituents unless such attachment or substitution would violate valence requirements or result in a chemically unstable compound. Examples of monocyclic heterocyclyl groups include oxiranyl, thiaranyl, aziridinyl (e.g., aziridin-1-yl and aziridin-2-yl), oxetanyl, thiatanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

"Heteroaryl" refers to unsaturated monocyclic aromatic groups and to polycyclic groups having at least one aromatic ring, each of the groups having ring atoms composed of carbon atoms and 1 to 4 heteroatoms independently selected from nitrogen (N), oxygen (O), and sulfur (S). Both the monocyclic and polycyclic groups generally have a specified number of carbon atoms as ring members (e.g., $C_{1-9}$-heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached to a parent group or to a substrate at any ring atom and may include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-a]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-a]pyridinyl, 7H-purinyl, indolizinyl, imidazo[1,2-a]pyridinyl, imidazo[1,5-a]pyridinyl, pyrazolo[1, 5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

"Halogen" ("halo" and "halogeno", which may be used interchangeably) in the context of the invention is fluorine, chlorine, iodine and bromine. Preference is given to fluorine.

"Halogenoalkyl", "halogenoalkenyl" and "halogenoalkynyl" (which may also be referred to as "haloalkyl", "haloalkenyl" and "haloalkynyl") refer, respectively, to alkyl, alkenyl, and alkynyl groups substituted with one or more halogen atoms, where alkyl, alkenyl, and alkynyl are defined above, and generally having a specified number of carbon atoms. Examples of halogenoalkyl groups include fluoromethyl, difluoromethyl, trifluoromethyl, chloromethyl, dichloromethyl, trichloromethyl, and the like.

"Hydroxyl" in the context of the invention is OH.

"Oxo" refers to a double bonded oxygen (=O).

"Alkoxy" in the context of the invention represents a straight-chain or branched alkoxy group having the particular number of carbon atoms specified. 1 to 6 carbon atoms are preferred. Examples include methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Particular preference is given to a linear or branched alkoxy group having 1 to 4 carbon atoms. Examples which may be mentioned as being preferred are methoxy, ethoxy, n-propoxy, 1-methylpropoxy, n-butoxy and isobutoxy.

A symbol * at a bond denotes the bonding site in the molecule.

"Substituted" when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution. When groups in the present compounds are substituted, the groups may be mono- or polysubstituted, unless specified otherwise. In the context of the present invention, all groups which occur more than once are defined independently of one another. Substitution by one, two or three identical or different substituents is preferred.

"About" or "approximately" when used in connection with a measurable numerical variable, refers to the indicated value of the variable and to all values of the variable that are within the experimental error of the indicated value or within ±10 percent of the indicated value, whichever is greater.

In a second aspect, the present invention provides compounds of the general formula (I) supra, wherein G is C(R$^5$), and the diastereomers, enantiomers, metabolites, salts, solvates or solvates of the salts thereof, for use in the treatment and/or prophylaxis of allergic and/or inflammatory diseases in animals.

In a third aspect, the present invention provides compounds of the general formula (I) supra, wherein L is —NH—, and the diastereomers, enantiomers, metabolites, salts, solvates or solvates of the salts thereof, for use in the treatment and/or prophylaxis of allergic and/or inflammatory diseases in animals.

In a fourth aspect, the present invention provides compounds of the general formula (I) supra, wherein L$^2$ is a bond, and the diastereomers, enantiomers, metabolites, salts, solvates or solvates of the salts thereof, for use in the treatment and/or prophylaxis of allergic and/or inflammatory diseases in animals.

In a fifth aspect, the present invention provides compounds of the general formula (I) supra wherein L$^1$ is —NH— and L$^2$ is a bond, according to the general formula (II):

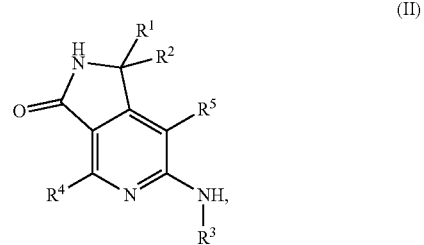

and wherein R$^1$, R$^2$, R$^3$, R$^4$ and R$^5$ independently have the meaning as defined in the embodiments according to any of the first to fourth aspect of the invention supra or to any of the sixth to fifteenth aspect of the invention below, and the diastereomers, enantiomers, metabolites, salts, solvates or solvates of the salts thereof, for use in the treatment and/or prophylaxis of allergic and/or inflammatory diseases in animals.

In a sixth aspect, the present invention provides compounds of the general formula (I) supra, wherein R$^1$ and R$^2$ are both hydrogen, and the diastereomers, enantiomers, metabolites, salts, solvates or solvates of the salts thereof, for use in the treatment and/or prophylaxis of allergic and/or inflammatory diseases in animals.

In a seventh aspect, the present invention provides compounds of the general formula (I) supra, wherein R$^3$ is C$_{3-8}$-cycloalkyl, optionally substituted with one to five substituents independently selected from halogen, oxo, —NO$_2$, —CN, R$^6$, and R$^7$, and the diastereomers, enantiomers, metabolites, salts, solvates or solvates of the salts thereof, for use in the treatment and/or prophylaxis of allergic and/or inflammatory diseases in animals.

In an eighth aspect, the present invention provides compounds of the general formula (I) supra, wherein R$^3$ is 2-amino-C$_{3-8}$-cycloalk-1-yl, optionally substituted with one to four substituents independently selected from halogen, oxo, —NO$_2$, —CN, R$^6$, and R$^7$, and the diastereomers, enantiomers, metabolites, salts, solvates or solvates of the salts thereof, for use in the treatment and/or prophylaxis of allergic and/or inflammatory diseases in animals.

In a ninth aspect, the present invention provides compounds of the general formula (I) supra, wherein R$^3$ is 2-amino-cyclohex-1-yl optionally substituted with one to four substituents independently selected from halogen, oxo, —NO$_2$, —CN, R$^6$, and R$^7$, and the diastereomers, enantiomers, metabolites, salts, solvates or solvates of the salts thereof, for use in the treatment and/or prophylaxis of allergic and/or inflammatory diseases in animals.

In a tenth aspect, the present invention provides compounds of the general formula (I) supra, wherein R$^4$ is a monocyclic C$_{2-4}$-heteroaryl optionally substituted with one to four substituents independently selected from halogen, oxo, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In an eleventh aspect, the present invention provides compounds of the general formula (I) supra, wherein $R^4$ is pyrazolyl optionally substituted with one to three substituents independently selected from halogen, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a twelfth aspect, the present invention provides compounds of the general formula (I) supra, wherein $R^4$ is pyrazol-4-yl optionally substituted with one to three substituents independently selected from halogen, oxo, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a thirteenth aspect, the present invention provides compounds of the general formula (I) supra, wherein $R^4$ is substituted with methyl, ethyl, cyclopropyl or $C_{1-2}$-halogenoalkyl having 1 to 5 halogen atoms, and the diastereomers, enantiomers, metabolites, salts, solvates or solvates of the salts thereof, for use in the treatment and/or prophylaxis of allergic and/or inflammatory diseases in animals.

In a fourteenth aspect, the present invention provides compounds of the general formula (I) supra, wherein $R^5$ is selected from hydrogen and halogen, and the diastereomers, enantiomers, metabolites, salts, solvates or solvates of the salts thereof, for use in the treatment and/or prophylaxis of allergic and/or inflammatory diseases in animals.

In a fifteenth aspect, the present invention provides compounds of the general formula (I) supra, wherein $R^5$ is selected from chlorine and fluorine, preferably fluorine, and the diastereomers, enantiomers, metabolites, salts, solvates or solvates of the salts thereof, for use in the treatment and/or prophylaxis of allergic and/or inflammatory diseases in animals.

The present invention especially provides the following compounds:
2-((1R,2S)-2-Aminocyclohexylamino)-4-(m-tolylamino)-6,7-dihydro-5H-pyrrolo[3,4-a']pyrimidin-5-one;
2-((1R,2S)-2-Aminocyclohexylamino)-4-(3-fluorophenylamino)-6,7-dihydro-5H-pyrrolo[3,4-d]pyrimidin-5-one;
2-((1R,2S)-2-Aminocyclohexylamino)-4-(3-chlorophenylamino)-6,7-dihydro-5H-pyrrolo[3,4-d]pyrimidin-5-one;
4-(1H-Indazo1-6-ylamino)-2-((1R,2S)-2-aminocyclohexylamino)-6,7-dihydro-5H-pyrrolo[3,4-d]pyrimidin-5-one;
2-((1R,2S)-2-aminocyclohexylamino)-4-(3-(trifluoromethyl)phenylamino)-6,7-dihydro-5H-pyrrolo[3,4-d]pyrimidin-5-one;
cis-2-(2-aminocyclohexylamino)-4-(3-(trifluoromethyl)phenylamino)-6,7-dihydro-5H-pyrrolo[3,4-d]pyrimidin-5-one;
2-(1-Methyl-1H-pyrazol-4-yl)-4-(m-tolylamino)-6,7-dihydro-5H-pyrrolo[3,4-d]pyrimidin-5-one;
2-(4-Ethylpiperazin-1-yl)-4-(m-tolylamino)-6,7-dihydro-5H-pyrrolo[3,4-d]pyrimidin-5-one;
2-(Cyclohexylamino)-4-(m-tolylamino)-6,7-dihydro-5H-pyrrolo[3,4-d]pyrimidin-5-one;
cis-2-(2-Hydroxycyclohexylamino)-4-(m-tolylamino)-6,7-dihydro-5H-pyrrolo[3,4-d]pyrimidin-5-one;
2-(3-Aminopiperidin-1-yl)-4-(m-tolylamino)-6,7-dihydro-5H-pyrrolo[3,4-d]pyrimidin-5-one;
6-((1R,2S)-2-Aminocyclohexylamino)-4-(m-tolylamino)-1H-pyrrolo[3,4-c]pyridin-3(2H)-one;
2-((1R,2S)-2-Aminocyclohexylamino)-4-(1-methyl-1H-pyrazol-4-yl)-6,7-dihydro-5H-pyrrolo[3,4-d]pyrimidin-5-one;
2-((1R,2S)-2-Aminocyclohexylamino)-4-(1-isobutyl-1H-pyrazol-4-yl)-6,7-dihydro-5H-pyrrolo[3,4-d]pyrimidin-5-one;
2-((1R,2S)-2-Aminocyclohexylamino)-4-phenyl-6,7-dihydro-5H-pyrrolo[3,4-d]pyrimidin-5-one;
2-((1R,2S)-2-Aminocyclohexylamino)-4-(benzo[b]thiophen-3-yl)-6,7-dihydro-5H-pyrrolo[3,4-d]pyrimidin-5-one;
2-((1R,2S)-2-Aminocyclohexylamino)-4-(1-ethyl-1H-pyrazol-4-yl)-6,7-dihydro-5H-pyrrol[3,4-d]pyrimidin-5-one;
2-((1R,2S)-2-Aminocyclohexylamino)-4-(1-benzyl-1H-pyrazol-4-yl)-6,7-dihydro-5H-pyrrolo[3,4-d]pyrimidin-5-one;
2-((1R,2S)-2-Aminocyclohexylamino)-4-(imidazo[1,2-a]pyridin-3-yl)-6,7-dihydro-5H-pyrrolo[3,4-d]pyrimidin-5-one;
2-((1R,2S)-2-Aminocyclohexylamino)-4-(1-propyl-1H-pyrazol-4-yl)-6,7-dihydro-5H-pyrrolo[3,4-d]pyrimidin-5-one;
2-((1R,2S)-2-Aminocyclohexylamino)-4-(1-(2-methoxyethyl)-1H-pyrazol-4-yl)-6,7-dihydro-5H-pyrrolo[3,4-d]pyrimidin-5-one;
4-(1H-Indazol-6-ylamino)-6-((1R,2S)-2-aminocyclohexylamino)-1H-pyrrolo[3,4-c]pyridin-3(2H)-one;
6-((1R,2S)-2-Aminocyclohexylamino)-4-(4-fluoro-3-methylphenylamino)-1H-pyrrolo[3,4-c]pyridin-3(2H)-one;
6-((1R,2S)-2-Aminocyclohexylamino)-7-fluoro-4-(m-tolylamin)-1H-pyrrolo[3,4-c]pyridin-3(2H)-one;
6-((1R,2S)-2-Aminocyclohexylamino)-4-(1-methyl-1H-pyrazol-4-yl)-1H-pyrrolo[3,4-c]pyridin-3(2H)-one;
6-((3R,4R)-3-Aminotetrahydro-2H-pyran-4-ylamino)-4-(1-methyl-1H-pyrazol-4-yl)-1H-pyrrolo[3,4-c]pyridin-3(2H)-one;
6-((1R,2S)-2-Aminocyclohexylamino)-7-fluoro-4-(1-methyl-1H-pyrazol-4-yl)-1H-pyrrolo[3,4-c]pyridin-3(2H)-one;
6-((1R,2S)-2-Aminocyclohexylamino)-7-chloro-4-(1-methyl-1H-pyrazol-4-yl)-1H-pyrrolo[3,4-c]pyridin-3(2H)-one;
6-((1R,2S)-2-Aminocyclohexylamino)-7-fluoro-4-(pyrazolo[1,5-a]pyridin-3-yl)-1H-pyrrolo[3,4-c]pyridin-3(2H)-one;
2-(2-(Aminomethyl)piperidin-1-yl)-4-(m-tolylamino)-6,7-dihydro-5H-pyrrolo[3,4-d]pyrimidin-5-one;
6-((1R,2S)-2-Aminocyclohexylamino)-4-(3-(methylsulfonyl)phenylamino)-1H-pyrrolo[3,4-c]pyridin-3(2H)-one;
6-((1R,2S)-2-Aminocyclopentylamino)-4-(3-(methylsulfonyl)phenylamino)-1H-pyrrolo[3,4-c]pyridin-3(2H)-one;
(R)-4-Methyl-2-(4-(3-(methylsulfonyl)phenylamino)-3-oxo-2,3-dihydro-1H-pyrrolo[3,4-c]pyridin-6-ylamino)pentanamide;
(R)-4-Methyl-2-(4-(1-methyl-1H-pyrazol-4-yl)-3-oxo-2,3-dihydro-1H-pyrrolo[3,4-c]pyridin-6-ylamino)pentanamide;
2-((1R,2S)-2-(Dimethylamino)cyclohexylamino)-4-(m-tolylamino)-6,7-dihydro-5H-pyrrolo[3,4-d]pyrimidin-5-one;
2-((1R,2S)-2-(Methylamino)cyclohexylamino)-4-(m-tolylamino)-6,7-dihydro-5H-pyrrolo[3,4-d]pyrimidin-5-one;

2'-((1R,2S)-2-Aminocyclohexylamino)-4'-(m-tolylamino)spiro[cyclopropane-1,7'-pyrrolo[3,4-d]pyrimidin]-5'(6'H)-one;

2-(2-Aminoethylamino)-4-(m-tolylamino)-6,7-dihydro-5H-pyrrolo[3,4-d]pyrimidin-5-one;

2-(2-Amino-2-methylpropylamino)-4-(m-tolylamino)-6,7-dihydro-5H-pyrrolo[3,4-d]pyrimidin-5-one;

2-(5-Oxo-4-(m-tolylamino)-6,7-dihydro-5H-pyrrolo[3,4-d]pyrimidin-2-ylamino)acetamide;

2-((2-Aminoethyl)(methyl)amino)-4-(m-tolylamino)-6,7-dihydro-5H-pyrrolo[3,4-d]pyrimidin-5-one;

2-(Pyrrolidin-2-ylmethylamino)-4-(m-tolylamino)-6,7-dihydro-SH-pyrrolo[3,4-d]pyrimidin-5-one;

2-(3-Aminopyrrolidin-1-yl)-4-(m-tolylamino)-6,7-dihydro-5H-pyrrolo[3,4-d]pyrimidin-5-one;

2-((1R,2S)-2-Aminocyclohexylamino)-4-(1,5-dimethyl-1H-pyrazol-4-yl)-6,7-dihydro-5H-pyrrolo[3,4-d]pyrimidin-5-one;

2-((1R,2S)-2-Aminocyclohexylamino)-4-(1H-indol-2-yl)-6,7-dihydro-5H-pyrrolo[3,4-d]pyrimidin-5-one;

2-((1R,2S)-2-Aminocyclohexylamino)-4-(1H-pyrazol-5-yl)-6,7-dihydro-5H-pyrrolo[3,4-d]pyrimidin-5-one;

2-(3-Aminopropyl)-4-(m-tolylamino)-6,7-dihydro-5H-pyrrolo[3,4-d]pyrimidin-5-one;

6-((1R,2S)-2-Aminocyclohexylamino)-4-(benzofuran-3-yl)-7-fluoro-1H-pyrrolo[34-c]pyridin-3(2H)-one;

6-((1R,2S)-2-aminocyclohexylamino)-7-fluoro-4-(imidazo[1,2-a]pyridin-3-yl)-1H-pyrrolo[3,4-c]pyridin-3(2H)-one;

6-((1R,2S)-2-aminocyclohexylamino)-4-(benzo[b]thiophen-3-yl)-7-fluoro-1H-pyrrolo[3,4-c]pyridin-3(2H)-one;

6-((1 S,2R)-2-Aminocyclohexylamino)-7-fluoro-4-(1-methyl-1H-pyrazol-4-yl)-1H-pyrrolo[3,4-c]pyridin-3(2H)-one;

(R)-6-(2-Amino-3-ethoxypropylamino)-4-(m-tolylamino)-1H-pyrrolo[3,4-c]pyridin-3(2H)-one;

(R)-6-(2-Amino-3-ethoxypropylamino)-7-fluoro-4-(m-tolylamino)-1H-pyrrolo[3,4-c]pyridin-3(2H)-one;

6-(2-Amino-3,3,3-trifluoropropylamino)-4-(m-tolylamino)-1H-pyrrolo[3,4-c]pyridin-3(2H)-one;

(R)-4-Methyl-2-(3-oxo-4-(m-tolylamino)-2,3-dihydro-1H-pyrrolo[3,4-c]pyridin-6-ylamino)pentanamide;

6-(cis-4-Aminotetrahydrofuran-3-ylamino)-4-(m-tolylamino)-1H-pyrrolo[3,4-c]pyridin-3(2H)-one;

6-((1R,2S)-2-Aminocyclohexylamino)-4-(1-ethyl-1H-pyrazol-4-yl)-1H-pyrrolo[3,4-c]pyridin-3(2H)-one;

6-((1R,2S)-2-Aminocyclohexylamino)-4-(1-ethyl-1H-pyrazol-4-yl)-7-fluoro-1H-pyrrolo[3,4-c]pyridin-3(2H)-one;

6-((1R,2S)-2-Aminocyclohexylamino)-4-(1-cyclopropyl-1H-pyrazol-4-yl)-1H-pyrrolo[3,4-c]pyridin-3(2H)-one;

6-((1R,2S)-2-Aminocyclohexylamino)-4-(1-(difluoromethyl)-1H-pyrazol-4-yl)-7-fluoro-1H-pyrrolo[3,4-c]pyridin-3(2H)-one;

6-((1R,2S)-2-Aminocyclohexylamino)-4-(1-cyclopropyl-1H-pyrazol-4-yl)-7-fluoro-1H-pyrrolo[3,4-c]pyridin-3(2H)-one;

cis-6-(2-Aminocyclohexylamino)-7-fluoro-4-(1-methyl-1H-pyrazol-4-yl)-1H-pyrrolo[3,4-c]pyridin-3(2H)-one;

6-((3R,4R)-3-Aminotetrahydro-2H-pyran-4-ylamino)-7-fluoro-4-(1-methyl-1H-pyrazol-4-yl)-1H-pyrrolo[3,4-c]pyridin-3(2H)-one;

6-(cis-Amino-4,4-difluorocyclopentylamino)-7-fluoro-4-(1-methyl-1H-pyrazol-4-yl)-1H-pyrrolo[3,4-c]pyridin-3(2H)-one;

6-(cis-2-Amino-3,3-difluorocyclohexylamino)-7-fluoro-4-(1-methyl-1H-pyrazol-4-yl)-1H-pyrrolo[3,4-c]pyridin-3(2H)-one;

6-(cis-2-Amino-3,3-difluorocyclohexylamino)-4-(1-(difluoromethyl)-1H-pyrazol-4-yl)-7-fluoro-1H-pyrrolo[3,4-c]pyridin-3(2H)-one;

6-(cis-2-amino-3,3-difluorocyclohexylamino)-4-(1-cyclopropyl-1H-pyrazol-4-yl)-7-fluoro-1H-pyrrolo[3,4-c]pyridin-3(2H)-one;

(R)-2-(7-Fluoro-4-(1-methyl-1H-pyrazol-4-yl)-3-oxo-2,3-dihydro-1H-pyrrolo[3,4-c]pyridin-6-ylamino)-4-methylpentanamide;

(R)-2-(4-(1-(Difluoromethyl)-1H-pyrazol-4-yl)-7-fluoro-3-oxo-2,3-dihydro-1H-pyrrolo[34-c]pyridin-6-ylamino)-4-methylpentanamide;

(R)-2-(4-(1-Cyclopropyl-1H-pyrazol-4-yl)-7-fluoro-3-oxo-2,3-dihydro-1H-pyrrolo[3,4-c]pyridin-6-ylamino)-4-methylpentanamide;

(R)-2-(4-(Benzofuran-3-yl)-7-fluoro-3-oxo-2,3-dihydro-1H-pyrrolo[3,4-c]pyridin-6-ylamino)-4-methylpentanamide;

(R)-2-(7-Fluoro-3-oxo-4-(pyrazolo[1,5-a]pyridin-3-yl)-2,3-dihydro-1H-pyrrolo[3,4-c]pyridin-6-ylamino)-4-methylpentanamide;

6-((1R,2S)-2-Aminocyclohexylamino)-7-chloro-4-(m-tolylamino)-1H-pyrrolo[3,4-c]pyridin-3(2H)-one;

6-((1R,2S)-2-Aminocyclohexylamino)-3-oxo-4-(m-tolylamino)-2,3-dihydro-1H-pyrrolo[3,4-c]pyridine-7-carbonitrile;

(R)-6-(2-Amino-3-methoxypropylamino)-4-(m-tolylamino)-1H-pyrrolo[3,4-c]pyridin-3(2H)-one;

(R)-6-(2-Amino-3-methoxypropylamino)-3-oxo-4-(m-tolylamino)-2,3-dihydro-1H-pyrrolo[3,4-c]pyridine-7-carbonitrile;

(R)-6-(2-Amino-3-methoxypropylamino)-7-fluoro-4-(m-tolylamino)-1H-pyrrolo[3,4-c]pyridin-3(2H)-one;

7-Acryloyl-6-((1R,2S)-2-aminocyclohexylamino)-4-(m-tolylamino)-1H-pyrrolo[3,4-c]pyridin-3(2H)-one;

6-((1R,2S)-2-Aminocyclohexylamino)-7-iodo-4-(m-tolylamino)-1H-pyrrolo[3,4-c]pyridin-3(2H)-one;

6-((1R,2S)-2-Aminocyclohexylamino)-7-(1H-pyrazol-4-yl)-4-(m-tolylamino)-1H-pyrrolo[3,4-c]pyridin-3(2H)-one;

6-(cis-2-Amino-3,3-difluorocyclohexylamino)-4-(m-tolylamino)-1H-pyrrolo[3,4-c]pyridin-3(2H)-one;

6-((1R,2S)-2-Aminocyclohexylamino)-7-(1-methyl-1H-pyrazol-5-yl)-4-(m-tolylamino)-1H-pyrrolo[3,4-c]pyridin-3(2H)-one;

6-((3R,4R)-3-Aminotetrahydro-2H-pyran-4-ylamino)-4-(m-tolylamin)-1H-pyrrolo[3,4-c]pyridin-3(2H)-one;

6-((3R,4R)-4-Aminotetrahydro-2H-pyran-3-ylamino)-4-(m-tolylamino)-1H-pyrrolo[3,4-c]pyridin-3(2H)-one;

tert-Butyl (1 S,2R)-2-(3-oxo-7-phenyl-4-(m-tolylamino)-2,3-dihydro-1H-pyrrolo[3,4-c]pyridin-6-ylamino)cyclohexylcarbamate;

6-((1R,2S)-2-Aminocyclohexylamino)-7-methyl-4-(m-tolylamino)-1H-pyrrolo[3,4-c]pyridin-3(2H)-one;

6-((3R,4R)-3-Aminotetrahydro-2H-pyran-4-ylamino)-7-fluoro-4-(m-tolylamino)-1H-pyrrolo[3,4-c]pyridin-3(2H)-one;

6-((1R,2S)-2-Aminocyclohexylamino)-7-methyl-4-(1-methyl-1H-pyrazol-4-yl)-1H-pyrrolo[3,4-c]pyridin-3(2H)-one;

(R)-6-(2-Amino-3-methoxypropylamino)-4-(1-methyl-1H-pyrazol-4-yl)-1H-pyrrolo[3,4-c]pyridin-3(2H)-one;

6-((3R,4R)-3-Aminotetrahydro-2H-pyran-4-ylamino)-7-fluoro-4-(pyrazolo[5-a]pyridin-3-yl)-1H-pyrrolo[3,4-c]pyridin-3(2H)-one;

6-((3R,4R)-3-Aminotetrahydro-2H-pyran-4-ylamino)-4-(1-(difluoromethyl)-1H-pyrazol-4-yl)-7-fluoro-1H-pyrrolo[3,4-c]pyridin-3(2H)-one;
6-((3R,4R)-3-Aminotetrahydro-2H-pyran-4-ylamino)-4-(benzofuran-3-yl)-7-fluoro-1H-pyrrolo[3,4-c]pyridin-3(2H)-one;
(S)-6-(3-Aminopyrrolidin-1-yl)-7-fluoro-4-(1-methyl-1H-pyrazol-4-yl)-1H-pyrrolo[3,4-c]pyridin-3(2H)-one;
(S)-6-(3-Aminopiperidin-1-yl)-7-fluoro-4-(1-methyl-1H-pyrazol-4-yl)-1H-pyrrolo[3,4-c]pyridin-3(2H)-one;
6-((1R,2S)-2-Aminocyclohexylamino)-7-fluoro-4-(1-isopropyl-1H-pyrazol-4-yl)-1H-pyrrolo[3,4-c]pyridin-3(2H)-one;
7-Fluoro-4,6-bis(1-methyl-1H-pyrazol-4-yl)-1H-pyrrolo[3,4-c]pyridin-3(2H)-one;
6-((1R,2S)-2-Aminocyclohexylamino)-7-bromo-4-(1-methyl-1H-pyrazol-4-yl)-1H-pyrrolo[3,4-c]pyridin-3(2H)-one;
2-((1R,2S)-2-Aminocyclohexylamino)-4-(1-(4-fluorophenyl)-1H-pyrazol-4-yl)-6,7-dihydro-5H-pyrrolo[3,4-d]pyrimidin-5-one;
(R)-6-(2-Amino-3-methoxypropylamino)-7-fluoro-4-(1-methyl-11H-pyrazol-4-yl)-1H-pyrrolo[3,4-c]pyridin-3(2H)-one;
6-((3R,4R)-3-Aminotetrahydro-2H-pyran-4-ylamino)-7-fluoro-4-(thiophen-3-yl)-1H-pyrrolo[3,4-c]pyridin-3(2H)-one;
6-((3R,4R)-3-Aminotetrahydro-2H-pyran-4-ylamino)-7-fluoro-4-(4-methylthiophen-2-yl)-1H-pyrrolo[3,4-c]pyridin-3(2H)-one;
6-((1R,2S)-2-Aminocyclohexylamino)-7-fluoro-4-(4-methylthiophen-2-yl)-1H-pyrrolo[3,4-c]pyridin-3(2H)-one;
6-((1R,2S)-2-Aminocyclohexylamino)-7-fluoro-4-(thiophen-3-yl)-1H-pyrrolo[3,4-c]pyridin-3(2H)-one;
(R)-2-(7-Fluoro-4-(1-methyl-1H-pyrazol-4-yl)-3-oxo-2,3-dihydro-1H-pyrrolo[3,4-c]pyridin-6-ylamino)-N,4-dimethylpentanamide;
6-((1R,2S)-2-Aminocyclohexylamino)-7-fluoro-4-(5-methylthiophen-2-yl)-1H-pyrrolo[3,4-c]pyridin-3(2H)-one;
(R)-2-(7-Fluoro-4-(4-methylthiophen-2-yl)-3-oxo-2,3-dihydro-1H-pyrrolo[3,4-c]pyridin-6-ylamino)-4-methylpentanamide;
(R)-2-(7-Fluoro-3-oxo-4-(thiophen-3-yl)-2,3-dihydro-1H-pyrrolo[3,4-c]pyridin-6-ylamino)-4-methylpentanamide;
(R)-2-(7-Fluoro-4-(5-methylthiophen-2-yl)-3-oxo-2,3-dihydro-1H-pyrrolo[3,4-c]pyridin-6-ylamino)-4-methylpentanamide;
6-((1R,2S)-2-Aminocyclohexylamino)-4-(2-aminothiazol-5-yl)-7-fluoro-1H-pyrrolo[3,4-c]pyridin-3(2H)-one;
(R)-2-(7-Fluoro-4-(furan-2-yl)-3-oxo-2,3-dihydro-1H-pyrrolo[3,4-c]pyridin-6-ylamino)-4-methylpentanamide;
(R)-2-(7-Fluoro-4-(furan-3-yl)-3-oxo-2,3-dihydro-1H-pyrrolo[3,4-c]pyridin-6-ylamino)-4-methylpentanamide;
(R)-2-(7-Fluoro-4-(furan-2-yl)-3-oxo-2,3-dihydro-1H-pyrrolo[3,4-c]pyridin-6-ylamino)-4-methylpentanamide;
(R)-2-(4-(5-Cyanothiophen-2-yl)-7-fluoro-3-oxo-2,3-dihydro-1H-pyrrolo[3,4-c]pyridin-6-ylamino)-4-methylpentanamide;
(R)-2-(4-(4-Cyanothiophen-2-yl)-7-fluoro-3-oxo-2,3-dihydro-1H-pyrrolo[34-c]pyridin-6-ylamino)-4-methylpentanamide;
(R)-2-(7-Fluoro-3-oxo-4-(thiazol-5-yl)-2,3-dihydro-1H-pyrrolo[3,4-c]pyridin-6-ylamino)-4-methylpentanamide;
(R)-2-(7-Fluoro-4-(isothiazol-5-yl)-3-oxo-2,3-dihydro-1H-pyrrolo[3,4-c]pyridin-6-ylamino)-4-methylpentanamide;
6-((1R,2S)-2-Aminocyclohexylamino)-7-fluoro-1,1-dimethyl-4-(1-methyl-1H-pyrazol-4-yl)-1H-pyrrolo[3,4-c]pyridin-3(2H)-one;
((1R,2S)-2-Aminocyclohexylamino)-7-fluoro-4-(1-methyl-1H-pyrazol-3-yl)-1H-pyrrolo[3,4-c]pyridin-3(2H)-one;
6-((1R,2S)-2-Aminocyclohexylamino)-7-fluoro-4-(2-methythiazol-5-yl)-1H-pyrrolo[3,4-c]pyridin-3(2H)-one;
6-((3R,4R)-3-Aminotetrahydro-2H-pyran-4-ylamino)-7-fluoro-4-(5-methylthiophen-2-yl)-1H-pyrrolo[3,4-c]pyridin-3(2H)-one;
6-((1R,2S)-2-Aminocyclohexylamino)-7-fluoro-1-methyl-4-(1-methyl-1H-pyrazol-4-yl)-1H-pyrrolo[3,4-c]pyridin-3(2H)-one;
(R)-2-(7-Fluoro-3-oxo-4-(thiophen-2-yl)-2,3-dihydro-1H-pyrrolo[3,4-c]pyridin-6-ylamino)-4-methylpentanamide;
6-((3R,4R)-3-Aminotetrahydro-2H-pyran-4-ylamino)-7-fluoro-4-(thiophen-2-yl)-1H-pyrrolo[3,4-c]pyridin-3(2H)-one;
6-((3R,4R)-3-Aminotetrahydro-2H-pyran-4-ylamino)-7-fluoro-4-(thiazol-5-yl)-1H-pyrrolo[3,4-c]pyridin-3(2H)-one;
6-((1R,2S)-2-Aminocyclohexylamino)-7-fluoro-4-(thiophen-2-yl)-1H-pyrrolo[3,4-c]pyridin-3(2H)-one;
6-((3R,4R)-3-Aminotetrahydro-2H-pyran-4-ylamino)-7-fluoro-4-(4-(trifluoromethyl)-1H-imidazol-1-yl)-1H-pyrrolo[3,4-c]pyridin-3(2H)-one;
6-((1R,2S)-2-Aminocyclohexylamino)-7-fluoro-4-(4-methyl-1H-imidazol-1-yl)-1H-pyrrolo[3,4-c]pyridin-3(2H)-one;
6-((3R,4R)-3-Aminotetrahydro-2H-pyran-4-ylamino)-7-fluoro-4-(3-methylisothiazol-5-yl)-1H-pyrrolo[3,4-c]pyridin-3(2H)-one;
6-((3R,4R)-3-Aminotetrahydro-2H-pyran-4-ylamino)-7-fluoro-4-(2-methylthiazol-5-yl)-1H-pyrrolo[3,4-c]pyridin-3(2H)-one;
(R)-2-(7-Fluoro-4-(2-methylthiazol-5-yl)-3-oxo-2,3-dihydro-1H-pyrrolo[34-c]pyridin-6-ylamino)-4-methylpentanamide;
6-((3R,4R)-3-Aminotetrahydro-2H-pyran-4-ylamino)-4-(5-chlorothiophen-2-yl)-7-fluoro-1H-pyrrolo[3,4-c]pyridin-3(2H)-one;
6-((3R,4R)-3-Aminotetrahydro-2H-pyran-4-ylamino)-4-(1-cyclopropyl-1H-pyrazol-4-yl)-7-fluoro-1H-pyrrolo[3,4-c]pyridin-3(2H)-one;

and the diastereomers, enantiomers, metabolites, salts, solvates or solvates of the salts thereof, for use in the treatment and/or prophylaxis of allergic and/or inflammatory diseases in animals.

In a very particular aspect of the present invention the compound according to formula (I) or (II) supra is a compound according to formula (III) or (IIIa)

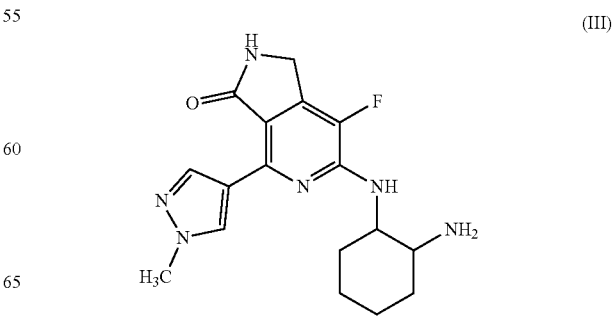

(III)

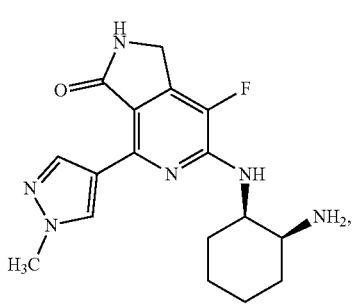

i.e., 6-((1R,2S)-2-aminocyclohexylamino)-7-fluoro-4-(1-methyl-1H-pyrazol-4-yl)-1H-pyrrolo[3,4-c]pyridine-3(2H)-one, or a diastereomer, enantiomer, metabolite, salt, solvate or solvate of a salt thereof, for use in the treatment and/or prophylaxis of allergic and/or inflammatory diseases in animals.

In another very particular aspect of the present invention the compound according to formula (I) or (II) supra is a compound according to formula (IV) or (IVa)

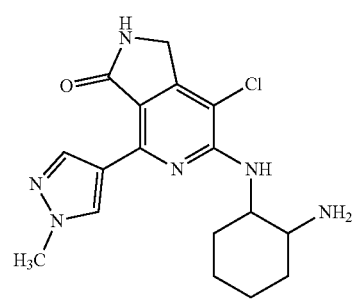

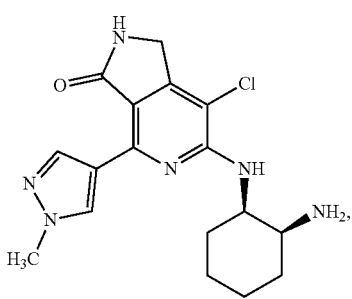

i.e. 6-((1R,2S)-2-Aminocyclohexylamino)-7-chloro-4-(1-methyl-1H-pyrazol-4-yl)-1H-pyrrolo[3,4-c]pyridin-3(2H)-one, or a diastereomer, enantiomer, metabolite, salt, solvate or solvate of a salt thereof, for use in the treatment and/or prophylaxis of allergic and/or inflammatory diseases in animals.

A further particular aspect of the present invention provides compounds of the general formula (I), (II), (III), (IIIa), (IV) or (IVa) supra, or a diastereomer, enantiomer, metabolite, salt, solvate or solvate of a salt thereof, for use in the treatment and/or prophylaxis of allergic and/or inflammatory diseases in animals, which act as dual SYK and JAK (SYK/JAK), SYK and IRAK 4 (SYK/IRAK4) or JAK and IRAK4 (JAK/IRAK4) inhibitor. Therein, in each case "JAK" relates to all or any combination of one or more of the JAK family, i.e. JAK1, JAK2, JAK3 and TYK2, unless explicitly stated otherwise.

A further particular aspect of the present invention provides compounds of the general formula (I), (II), (III), (IIIa), (IV) or (IVa) supra, or a diastereomer, enantiomer, metabolite, salt, solvate or solvate of a salt thereof, for use in the treatment and/or prophylaxis of allergic and/or inflammatory diseases in animals, which act as ternary inhibitor of SYK and JAK and IRAK4 (SYK/JAK/IRAK4 inhibitor). Therein, in each case "JAK" relates to all or any combination of one or more of the JAK family, i.e. JAK1, JAK2, JAK3 and TYK2, unless explicitly stated otherwise.

In the Following, Further Aspects of the Present Invention are Described:

In a further aspect, the present invention provides compounds of the general formula (I) supra, wherein G is N, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $L^1$ is a bond, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $L^2$ is —NH—, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^3$ is $C_{2-6}$-alkyl optionally substituted with one to five substituents independently selected from halogen, oxo, —NO$_2$, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^3$ is 2-amino-$C_{2-6}$-alk-1-yl optionally substituted with one to four substituents independently selected from halogen, oxo, —NO$_2$, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^3$ is 2-aminoethan-1-yl optionally substituted with one to four substituents independently selected from halogen, oxo, —NO$_2$, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^3$ is 2-amino-2-oxoethan-1-yl optionally substituted with one or two substituents independently selected from halogen, oxo, —NO$_2$, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^3$ is $C_{2-5}$-heterocyclyl optionally substituted with one to five substituents independently selected from halogen, oxo, —$NO_2$, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^3$ is $C_{2-5}$-heterocyclyl substituted with an amino and optionally substituted with one to four additional substituents independently selected from halogen, oxo, —$NO_2$, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^3$ is 3-aminotetrahydro-2H-pyran-4-yl optionally substituted with one to four substituents independently selected from halogen, oxo, —$NO_2$, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^3$ is $C_{2-5}$-heterocyclyl or an amino-substituted $C_{2-5}$-heterocyclyl, each optionally substituted with one to five or from one to four substituents, respectively, independently selected from halogen, oxo, —$NO_2$, —CN, $R^6$, and $R^7$, wherein one of the heteroatoms of the heterocyclyl moiety is directly attached to $L^1$, and $L^1$ is a bond, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^4$ is selected from $C_{6-14}$-aryl and $C_{1-9}$-heteroaryl, each optionally substituted with one to five substituents independently selected from halogen, oxo, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^4$ is phenyl optionally substituted with one to five substituents independently selected from halogen, oxo, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^4$ is $C_{1-9}$-heteroaryl optionally substituted with one to five substituents independently selected from halogen, oxo, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^4$ is selected from pyrrolyl, furanyl, thiopheneyl, pyrazolyl, imidazolyl, isoxazolyl, oxazolyl, isothiazolyl, and thiazolyl, each optionally substituted with one to three substituents independently selected from halogen, oxo, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^4$ is selected from thiopheneyl, pyrazolyl, isothiazolyl, and thiazolyl, each optionally substituted with one to three substituents independently selected from halogen, oxo, —CN, $R^6$, and $R^7$, and the diastereomers, enantiomers, metabolites, salts, solvates or solvates of the salts thereof, for use in the treatment and/or prophylaxis of allergic and/or inflammatory diseases in animals.

In a further aspect, the present invention provides compounds of the general formula (I) supra, wherein $R^5$ is $C_{1-5}$-heteroaryl optionally substituted with one to four substituents independently selected from halogen, —$NO_2$, —CN, $C_{1-4}$-alkyl, $C_{2-4}$-alkenyl, $C_{2-4}$-alkynyl, $C_{1-4}$-halogenoalkyl having 1 to 5 halogen atoms, and $R^{10}$, and the diastereomers, enantiomers, metabolites, salts, solvates or solvates of the salts thereof, for use in the treatment and/or prophylaxis of allergic and/or inflammatory diseases in animals.

Further particular aspects of the present invention relate to any of the aspects of the present invention supra for use in the treatment and/or prophylaxis of allergic and/or inflammatory diseases in domestic animals and/or in farm animals.

Further particular aspects of the present invention relate to any of the aspects of the present invention supra for use in the treatment and/or prophylaxis of Atopic Dermatitis, FAD, inflammatory bowel disease, osteoarthritis and inflammatory pain, non-infectious recurrent airway disease, insect hypersensitivity, asthma, respiratory disease, mastitis and endometritis in animals.

Further particular aspects of the present invention relate to any of the aspects of the present invention supra for use in the treatment and/or prophylaxis of Atopic Dermatitis and Flea Allergy Dermatitis in dogs or cats, in particular in dogs.

Further particular aspects of the present invention relate to a composition comprising at least one of the compounds of the formulae (I), (II), (III), (IIIa), (IV) or (IVa) as defined in any of the aspects of the present invention supra in combination with an inert, non-toxic, pharmaceutically suitable excipient, for use in the treatment and/or prophylaxis of allergic and/or inflammatory diseases in animals, such as in particular for the use in the treatment and/or prophylaxis of Atopic Dermatitis, Flea Allergy Dermatitis, inflammatory bowel disease, osteoarthritis and inflammatory pain, non-infectious recurrent airway disease, insect hypersensitivity, asthma, respiratory disease, mastitis and endometritis in animals, more particularly for the use in the treatment and/or prophylaxis of CAD and FAD, in each case preferably for treating domestic animals and/or in farm animals, more preferably for treating dogs or cats, very particularly for treating dogs.

The compounds (I), (II), (III), (IIIa), (IV) and (IVa) according to the present invention can be prepared as described e.g. in WO 2011/079051 A1 and WO 2016/097862 A2.

As described previously, the intracellular enzyme interleukin-1 receptor-associated kinase 4 (IRAK4), as well as the intracellular non-receptor tyrosine kinases spleen tyrosine kinase (SYK) and the Janus kinases (JAK) each play an integral part in the signaling pathway of receptors activated by cytokines and TLR ligands that are implicated in inflammatory processes. Specially, IRAK4, SYK and/or JAK are involved in the signaling of allergic processes. Such allergic processes play a key role in the pathogenesis of allergic skin diseases, like atopic dermatitis.

Hence, as IRAK4, SYK and/or JAK are a critical part of the activation of immune cells and signaling pathways activated by a number of cytokines and TLR ligands as well as increased IgE levels, inhibition of IRAK4, SYK and/or JAK is a comprehensive and innovative therapeutic strategy for the treatment of allergic skin diseases such as atopic dermatitis. Moreover, in companion animals (especially dogs and cats) both Atopic Dermatitis and FAD are appropriate indications since both diseases are comprised of Type I hypersensitivity that involves IgE antibodies, Th2 cells/cytokines, mast cells and eosinophils. In addition, CAD and FAD can be comprised of Type IV hypersensitivity in which Th1 cells/cytokines as IL-1 and IL-18 are involved.

The present compounds act as inhibitors of IRAK4 and/or SYK and/or JAK kinases and therefore have an unforeseeable useful pharmacological activity spectrum in the treatment and/or prophylaxis of allergic and/or inflammatory diseases in animals. Therein, in each case "JAK" relates to all or any combination of one or more of the JAK family, i.e. JAK1, JAK2, JAK3 and TYK2, unless explicitly stated otherwise.

The term "animal(s)" in the context of the present invention comprises in particular mammals, wherein humans shall not be covered by the term "animal(s)" or "mammal(s)" according to the present invention. This means that in the use according to the present invention the treatment of humans is excluded.

Further preference is given to compounds of the formula (I), (II), (III), (IIIa), (IV) or (IVa) supra, or the compounds particularly mentioned above, for use in the treatment and/or prophylaxis of allergic and/or inflammatory diseases in domestic animals, particularly in cats and dogs, and more particularly in dogs.

The term "domestic animals" in this context includes, for example, mammals, such as hamsters, guinea pigs, rats, mice, chinchillas, ferrets or in particular dogs, cats; cage birds; reptiles; amphibians or aquarium fish.

Further preference is given to compounds of the formula (I), (II), (III), (IIIa), (IV) or (IVa) supra, or the compounds particularly mentioned above, for use in the treatment and/or prophylaxis of allergic dermatitis in domestic animals, particularly canine and feline allergic dermatitis, and more particularly CAD. Further preference is given to compounds of the formula (I), (II), (III), (IIIa), (IV) or (IVa) supra, or the compounds particularly mentioned above, for use in the treatment and/or prophylaxis of allergic and/or inflammatory diseases in farm animals, particularly in sheep, goats, horses, cattle and pigs, and more particularly in cattle and pigs.

The term "farm animals" in this context includes, for example, mammals, such as horses, sheep, goats, buffaloes, reindeers, fallow deers or in particular cattle or pigs.

Further preference is given to compounds of the formula (I), (II), (III), (IIIa), (IV) or (IVa) supra, or the compounds particularly mentioned above, for use in a method for treatment and/or prophylaxis of atopic dermatitis, FAD, inflammatory bowel disease, osteoarthritis and inflammatory pain, non-infectious recurrent airway disease, insect hypersensitivity, asthma, respiratory disease, mastitis and endometritis in animals, particularly of CAD and FAD.

Particular preference is given to compounds of the formula (I), (II), (III), (IIIa), (IV) or (IVa) supra, or the compounds particularly mentioned above, for use in a method for treatment and/or prophylaxis of Atopic Dermatitis, FAD in dogs or cats, inflammatory bowel disease in dogs or cats, osteoarthritis and inflammatory pain in dogs, cats, horses or cattle, non-infectious recurrent airway disease in horses, insect hypersensitivity in horses, feline asthma, bovine respiratory disease, mastitis in cattle, endometritis in cattle, and swine respiratory disease.

Very particular preference is given to compounds of the formula (I), (II), (III), (IIIa), (IV) or (IVa) supra, or the compounds particularly mentioned above, for use in a method for treatment and/or prophylaxis of Atopic Dermatitis and Flea Allergy Dermatitis in dogs or cats, more particularly in dogs.

Further very particular preference is given to compounds of the formula (I), (II), (III), (IIIa), (IV) or (IVa) supra, or the compounds particularly mentioned above, for use in a method for treatment and/or prophylaxis of osteoarthritis and inflammatory pain in cattle, bovine respiratory disease, mastitis in cattle, endometritis in cattle, and swine respiratory disease.

In particular, the compound according to formula (IIIa) supra has been evaluated in vivo in a study to establish the effects of compounds of the formula (I), (II), (III), (IIIa), (IV) or (IVa) supra in the treatment of clinical signs associated with canine allergic dermatitis, particularly CAD, in a House Dust Mite model. The compound according to formula (IIIa) supra significantly reduced clinical signs of CAD like skin edema and erythema. This example is illustrated by Tables 1 and 2 and FIGS. 1 and 2.

Hence, the present compounds demonstrate reduction of characteristic clinical signs of canine allergic dermatitis, therefore indicating a therapeutic benefit of such compound examples in canine allergic dermatitis, particularly in CAD. Activity in treating the clinical signs of CAD can be estimated for a reduction rate of >70% % when administered at 2 mg/kg twice per day.

The prophylaxis and/or treatment of pruritus and pain, especially of acute, chronic, inflammatory and neuropathic pain in animals, is also provided by the present compounds.

In addition, the present compounds are suitable for the treatment and/or prophylaxis of pain disorders, especially of acute, chronic, inflammatory and neuropathic pain in animals. This preferably includes hyperalgesia, allodynia, pain from arthritis (such as osteoarthritis, rheumatoid arthritis and spondyloarthritis), post-operative pain, pain from interstitial cystitis, pain caused by spinal cord injuries, inflammation-induced pain, cancer pain, burn-induced pain and chronic pain.

It must be acknowledged as particularly surprising that the compounds of the present invention exhibit the shown efficacy in the treatment and/or prophylaxis as described herein in animals. Although said indications have already been described in the prior art, e.g. in WO2011/079051 A1 and WO2016/097862 A2, therein only their activity as SYK inhibitor has been mentioned and the specific indications of the present invention have only been mentioned generally without providing any data making the efficacy in said specific indications at all credible. Even more, WO2011/079051 A1, WO2016/097862 A2 and Lam et al., Bioorganic & Medicinal Chemistry Letters 2016 all focus on the treatment of humans and the treatment and/or prophylaxis of the specific indication as described herein in animals (excluding humans) cannot be concluded therefrom as the underlying pathogenesis, pathophysiology and metabolic and regulatory pathways and mechanisms are different in humans and in animals.

The efficacy of the compounds of present invention in animals have been shown in tests as further described in Examples 1 and 2.

The present invention further also provides a method for treatment and/or prevention of disorders in animals, especially the disorders mentioned above, using an effective amount of at least one of the presented compounds.

Preference is given to a method for treatment and/or prevention of allergic and/or inflammatory diseases in animals by administering an effective amount of at least a compound of the present formula (I), (II), (III), (IIIa), (IV) or (IVa) each as defined supra to an animal in need thereof.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present compounds can be used alone or, if required, in combination with other active ingredients. The present invention further provides medicaments containing at least one of the present compounds and one or more further active ingredients, for treatment and/or prevention of allergic and/or inflammatory diseases in animals. Preferred examples of active ingredients suitable for combinations include:

General mention may be made of active ingredients such as antibacterial (e.g. penicillins, vancomycin, ciprofloxacin), antiviral (e.g. aciclovir, oseltamivir) and antimycotic (e.g. naftifin, nystatin) substances and gamma globulins, immunomodulatory and immunosuppressive compounds such as cyclosporin, Methotrexat®, TNF antagonists, IL-1 inhibitors, phosphodiesterase inhibitors, Jak/STAT inhibitors, leflunomid, cyclophosphamide, rituximab, belimumab, tacrolimus, rapamycin, mycophenolate mofetil, interferons, corticosteroids (e.g. prednisone, prednisolone, methylprednisolone, hydrocortisone, betamethasone), cyclophosphamide, azathioprine and sulfasalazine; paracetamol, non-steroidal anti-inflammatory substances (NSAIDS) (e.g. aspirin, ibuprofen, naproxen, etodolac, celecoxib, colchicine).

In addition to those mentioned above, the inventive IRAK4, SYK and/or JAK inhibitors can also be combined with the following active ingredients:

substances for treatment of pulmonary disorders, for example beta-2-sympathomimetics, anticholinergics, methylxanthines, leukotriene receptor antagonists, PDE-4 (phosphodiesterase type 4) inhibitors, methotrexate, IgE antibodies, azathioprine and cyclophosphamide, cortisol-containing preparations; substances for treatment of osteoarthritis such as non-steroidal anti-inflammatory substances (NSAIDs). In addition to the two therapies mentioned, methotrexate and biologics for B-cell and T-cell therapy should be mentioned for rheumatoid disorders, for example rheumatoid arthritis, spondyloarthritis and juvenile idiopathic arthritis. Neurotrophic substances such as acetylcholinesterase inhibitors, MAO (monoaminooxidase) inhibitors, interferons und anticonvulsives; active ingredients for treatment of cardiovascular disorders such as beta-blockers, ACE inhibitors, angiotensin receptor blockers, diuretics, calcium channel blockers, statins; anti-diabetic drugs, active ingredients such as antibiotics, anti-diarrhoea drugs, or laxatives for treatment of chronic inflammatory bowel diseases. Immunosuppressants, such as glucocorticoids and non-steroidal anti-inflammatory substances (NSAIDs), cortisone, chloroquine, cyclosporine, azathioprine, belimumab, rituximab, cyclophosphamide for treatment of lupus erythematosus. Vitamin D3 analogues, for example calcipotriol, tacalcitol or calcitriol, salicylic acid, urea, ciclosporine, methotrexate, efalizumab for dermatological disorders.

Mention should also be made of medicaments comprising at least one of the present compounds and one or more further active ingredients for the inventive use, especially EP4 inhibitors (prostaglandin E2 receptor 4 inhibitors), P2X3 inhibitors (P2X purinoceptor 3), PTGES inhibitors (prostaglandin E synthase inhibitors) or AKR1C3 inhibitors (aldo-keto reductase family 1 member C3 inhibitors), for treatment and/or prevention of the aforementioned disorders.

The present compounds can act systemically and/or locally. For this purpose, they can be administered in a suitable manner, for example by the oral, parenteral, pulmonal, nasal, sublingual, lingual, buccal, rectal, dermal, transdermal or conjunctival route, via the ear or as an implant or stent.

The present compounds can be administered in administration forms suitable for these administration routes.

Suitable administration forms for oral administration are those which work according to the prior art and release the present compounds rapidly and/or in a modified manner and which contain the present compounds in crystalline and/or amorphous and/or dissolved form, for example tablets (uncoated or coated tablets, for example with gastric juice-resistant or retarded-dissolution or insoluble coatings which control the release of the present compound), tablets or films/oblates which disintegrate rapidly in the oral cavity, films/lyophilizates, capsules (for example hard or soft gelatin capsules), sugar-coated tablets, chewables (for example soft chewables), granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, pour-ons, transdermal therapeutic systems (e.g. patches), milk, pastes, foams, sprinkling powders, implants or stents.

Preference is given to oral or parenteral administration, especially oral administration.

The present compounds can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

The present invention further provides medicaments which comprise at least one present compound, typically together with one or more inert, nontoxic, pharmaceutically suitable excipients, for use in a method for treatment and/or prophylaxis of allergic and/or inflammatory diseases in animals.

The following examples illustrate the invention; however, the invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

EXAMPLES

Example 1: Canine IRAK4 Kinase Assay

The IRAK4-inhibitory activity of the present compounds on canine IRAK4 is measured in the Irak4 TR-FRET assay (TR-FRET=Time Resolved Fluorescence Resonance Energy Transfer) described hereinafter.

Recombinant fusion protein from N-terminal HIS (Polyhistidine) and canine IRAK4, expressed in baculovirus-infected insect cells (Hi5, BTI-TN-5B1-4, cell line purchased from Invitrogen, catalogue No. B855-02) and purified via affinity chromatography, is used as enzyme. The substrate used for the kinase reaction is the biotinylated peptide biotin-Ahx-KKARFSRFAGSSPSQASFAEPG (C-terminus in amide form) which can be purchased, for example, from Biosyntan GmbH (Berlin-Buch).

For the assay, 11 different concentrations in the range from 20 µM to 0.073 nM are prepared from a 2 mM solution of the test substance in DMSO. 50 nl of the respective solution are pipetted into a black low-volume 384-well microtitre plate (Greiner Bio-One, Frickenhausen, Germany), 2 µl of a solution of IRAK4 in assay buffer [50 mM HEPES pH 7.5, 5 mM MgCl2, 1.0 mM dithiothreitol, 30 µM activated sodium orthovanadate, 0.1% (w/v) of bovine gamma-globulin (BGG) 0.04% (v/v) nonidet-P40 (Sigma)] are added and the mixture is incubated for 15 min to allow prebinding of the substances to the enzyme prior to the kinase reaction. The kinase reaction is then started by addition of 3 µl of a solution of adenosine triphosphate (ATP, 1.67 mM=final concentration in 5 µl of assay volume: 1 mM) and peptide substrate (0.83 µM=final concentration in 5 µl assay volume: 0.5 µM) in assay buffer, and the resulting mixture is incubated at 22° C. for the reaction time of 45 min. The concentration of the IRAK4 is adjusted to the respective activity of the enzyme and set such that the assay is carried out in the linear range. Typical concentrations are in the order of about 0.1 nM. The reaction is stopped by addition of 5 µl of a solution of TR-FRET detection reagents [0.1 µM streptavidin-XL665 (Cisbio Bioassays; France, catalogue No. 610SAXLG)] and 1.5 nM anti-phosphoserine antibody [Merck Millipore, "STK Antibody", catalogue No. 35-002] and 0.6 nM LANCE EU-W1024-labelled anti-mouse-IgG antibody (Perkin-Elmer, product No. AD0077; alternatively, it is possible to use a terbium cryptate-labelled anti-mouse-IgG antibody from Cisbio Bioassays) in aqueous EDTA solution (100 mM EDTA, 0.4% [w/v] bovine serum albumin [BSA] in 25 mM HEPES pH 7.5).

The resulting mixture is incubated at 22° C. for 1 h to allow formation of a complex of the biotinylated phosphorylated substrate and the detection reagents. The amount of the phosphorylated substrate is then evaluated by measuring the resonance energy transfer from europium chelate-labelled anti-mouse-IgG antibody to streptavidin-XL665. To this end, the fluorescence emissions at 620 nm and 665 nm is measured after excitation at 350 nm in a TR-FRET measuring instrument, for example a Rubystar (BMG Labtechnologies, Offenburg, Germany) or a Viewlux (Perkin-Elmer). The ratio of the emissions at 665 nm and 622 nm is taken as a measure of the amount of phosphorylated substrate. The data are normalized (enzyme reaction without test substance=0% inhibition; all other assay components but no enzyme=100% inhibition). Typically, the test substances are tested on the same microtitre plates at 11 different concentrations in the range from 20 µM to 0.073 nM (20 µM, 5.7 µM, 1.6 µM, 0.47 µM, 0.13 µM, 38 nM, 11 nM, 3.1 nM, 0.89 nM, 0.25 nM and 0.073 nM). The dilution series are prepared prior to the assay (2 mM to 7.3 nM in 100% DMSO) by serial dilutions. The $IC_{50}$ values are calculated by a 4-parameter fit.

Example 2 Radiometric Protein Kinase Assay

The compounds of the instant invention described in the Examples were tested by the assays described below and were found to have kinase inhibitory activity.

A radiometric protein kinase assay was used for measuring the kinase activity of the Dog (*Canis lupus familiaris*) IRAK4, JAK1, JAK2, SYK kinases. All kinase assays were performed in 96-well FlashPlates in a 50 µl reaction volume. The reaction cocktail was pipetted in four steps in the following order:

20 µl of assay buffer (standard buffer)
5 ml of test compound (in 10% DMSO)
20 µl enzyme/substrate mix
µl of ATP solution (in H2O) The reaction cocktails were incubated at 30° C. for 60 minutes. The reaction was stopped with 50 µl of 2% (v/v) H3PO4, plates were aspirated and washed two times with 200 µl 0.9% (w/v) NaCl. Incorporation of 33Pi was determined with a microplate scintillation counter.

$IC_{50}$ calculation: the residual activity (in %) for each well of a particular plate was calculated by using the following formula: Res. Activity (%)=100×[(cpm of compound−low control)/(high control−low control)]

The residual activities for each concentration and the compound IC50 values were calculated using Quattro Workflow V3.1.1 (Quattro Research GmbH, Munich, Germany; www.quattro-research.com). The fitting model for the $IC_{50}$ determinations was "Sigmoidal response (variable slope)" with parameters "top" fixed at 100% and "bottom" at 0%. The fitting method used was a least-squares fit.

Materials: The dog (*Canis lupus familiaris*) protein kinases IRAK4, JAK1, JAK2 and SYK had been recombinantly expressed in Sf9 insect cells and purified by affinity chromatography. The standart buffer for all protein kinases assays contained 70 mM HEPES-NaOH pH 7.5, 3 mM MgCl2, 3 mM MnCl2, 3 µM Na-orthovanadate, 1.2 mM DTT, 50 µg/ml PEG20000, ATP (variable concentrations, corresponding to the apparent ATP-Km of the respective kinase at indicated concentration in ng/50 µM (IRAK4: 10 µM ATP, Kinase conc: 20 ng/50 µl, substrate Histone H2B 1 µg/50 µl; JAK1: 3 µM ATP, Kinase conc: 200 ng/50 µl, substrate RBER-IRStide 2 µg/50 µl; JAK2: 0.3 µM, Kinase conc: 200 ng/50 g, substrate PolyAEKY 0.125 µg/50 µl 1; SYK: 1 µM ATP, Kinase conc: 100 ng/50 µl, substrate PolyEY 0.125 µg/50 µl)

TABLE 1

IC50 values masured on different dog protein kinases for compound IIIa and IVa

| Compound | $IC_{50}$ IRAK4 [M] | $IC_{50}$ JAK1 [M] | $IC_{50}$ JAK2 [M] | $IC_{50}$ SYK [M] |
|---|---|---|---|---|
| IIIa | 1.77E−08 | 3.07E−06 | 4.83E−06 | 4.62E−06 |
| IVa | 1.02E−08 | 4.66E−07 | 6.24E−07 | 3.23E−07 |

Example 3: In Vivo Model of House Dust Mite Induced Canine Allergic Dermatitis

To evaluate the potential anti-allergic/anti-inflammatory efficacy of the compounds of the formula (I), (II), (III) or (IIIa) supra a model of house dust mites (HDM)-sensitized Beagle dogs was used. Therein, HDM-sensitization consisted of a series of subcutaneous injections of HDM antigen (10 µg, Greer Laboratories, Lenoir, N.C., USA) and Alhydrogel® (0.2 mL, InvivoGen, San Diego, Calif. 921221, USA) as adjuvant in time intervals of approximately two weeks. The sensitization process was monitored and confirmed by intradermal skin testing. Once the dogs were positive to HDM skin intradermal testing, one month apart from the last sensitization, HDM antigen (135 µg) was topically applied and pricked into the skin (with 2 mm long micro needles) of the adult Beagle dogs in the inner part of the posterior legs and the effect of the example compound according to formula (IIIa) supra and of oclacitinib (Apoquel®, Zoetis) on signs of allergic dermatitis, e.g. erythema and edema, was examined. There were 3 studies carried out. In all the studies there were 2 groups of 5 to 7 animals each: 1 untreated control group and 1 group treated with either the compound according to formula (IIIa) supra or Apoquel®. The control group was not treated while the group treated with the compound according to formula (IIIa) supra was orally treated with gelatin capsules containing the compound according to formula (IIIa) supra and Ac-Di-Sol; the group receiving Apoquel®, received the commercially available tablets. The administration of the compound according to formula (IIIa) supra or Apoquel® started 5 days before the challenge with HDM antigen and continued until 2 days after the challenge. The treatment frequency was twice daily; in the case of the compound according to formula (IIIa) supra the dose was of 0.8 mg/kg body weight in the first study and of 2 mg/kg body weight in the second study; in the case of Apoquel®, the dose was administered as per label (0.4-0.6 mg/kg). Starting 30 min after challenge and at different time points for 48 h, erythema and edema were evaluated using VAS (Visual Analogue Scale) in the 2 groups. Plasma samples were analyzed to determine exposure to the compound in relationship to the clinical evaluations. Edema and erythema were significantly reduced after treatment with the compound according to formula (IIIa) supra. This is illustrated by Tables 1 and 2, and by FIGS. 1 and 2.

Activity of Apoquel® in treating the clinical signs of erythema and edema can be estimated for a reduction rate of 23% and 21%, respectively (when compared to the control group). In the case of the compound according to formula (IIIa) supra, the activity in treating the clinical signs of erythema and edema at 0.8 mg/kg BID can be estimated for reduction rates of 28-100% and 39-100%, respectively. When the compound according to formula (IIIa) supra was administered at 2 mg/kg BID, the activity in treating the clinical signs of erythema and edema can be estimated for reduction rates of 69-100% and 75-100%, respectively. When Apoquel® was administered at 0.4-0.6 mg/kg BID, the activity in treating the clinical signs of erythema and edema can be estimated for reduction rates of 19-48% and −21-56%, respectively. The dose regimen of Apoquel® as per label indicates that treatment needs to be given BID at 0.4-0.6 mg/kg for the first 2 weeks and then it needs to be reduced to once daily (SID) at the same dose range. This change from BID and SID is based on the toxicological/safety profile of the compound driven by the highly selective JAK-inhibition resulting in immunosuppression. In the case of the compound according to formula (IIIa) supra, since JAK inhibition seems to be a secondary although key component in its efficacy (see inhibition kinase panel driven by SYK), this gives a competitive advantage to the compound according to formula (IIIa) supra for the treatment of CAD and allows to increase the dose. The higher efficacy of the compound according to formula (IIIa) supra compared to oclacitinib (active ingredient of Apoquel®) seems to rely on the inhibition of various signaling pathways instead of solely inhibition of JAK targeted by oclacitinib.

TABLE 2

Percentage of reduction of Erythema (compared to the untreated control; based on median values) after treatment with either the compound according to formula (IIIa) supra at either 0.8 mg/kg and 2 mg/kg BID or Apoquel ® at 0.4-0.6 mg/kg BID

| Percentage of reduction of Erythema at different times post-challenge (hours) (based on median values) | Compound according to formula (IIIa) supra at either 0.8 mg/kg BID | Compound according to formula (IIIa) supra at 2 mg/kg BID | Apoquel ® at 0.4-0.6 mg/kg BID |
|---|---|---|---|
| 0.5 | 33% | 74% | 22% |
| 1 | 63% | 76% | 48% |
| 4 | 30% | 75% | 48% |
| 6 | 28% | 76% | 41% |
| 24 | 43% | 69% | 19% |
| 48 | 100% | 100% | 44% |

These results show that the compound according to formula (IIIa) supra achieves a comparative reduction of erythema in the CAD model (expressed as % compared the control group) after treatment of up to >75% when administered at 2 mg/kg BID (FIG. 1).

TABLE 3

Percentage of reduction of Edema (compared to the untreated control; based on median values) after treatment with either the compound according to formula (IIIa) supra at either 0.8 mg/kg and 2 mg/kg BID or Apoquel ® at 0.4-0.6 mg/kg BID

| Percentage of reduction of Edema at different times post-challenge (hours) (based on median values) | Compound according to formula (IIIa) supra at either 0.8 mg/kg BID | Compound according to formula (IIIa) supra at 2 mg/kg BID | Apoquel ® at 0.4-0.6 mg/kg BID |
|---|---|---|---|
| 0.5 | 41% | 76% | −21% |
| 1 | 52% | 81% | 35% |
| 4 | 39% | 75% | 39% |
| 6 | 49% | 79% | 32% |
| 24 | 41% | 75% | 25% |
| 48 | 100% | 100% | 56% |

Figure 2:
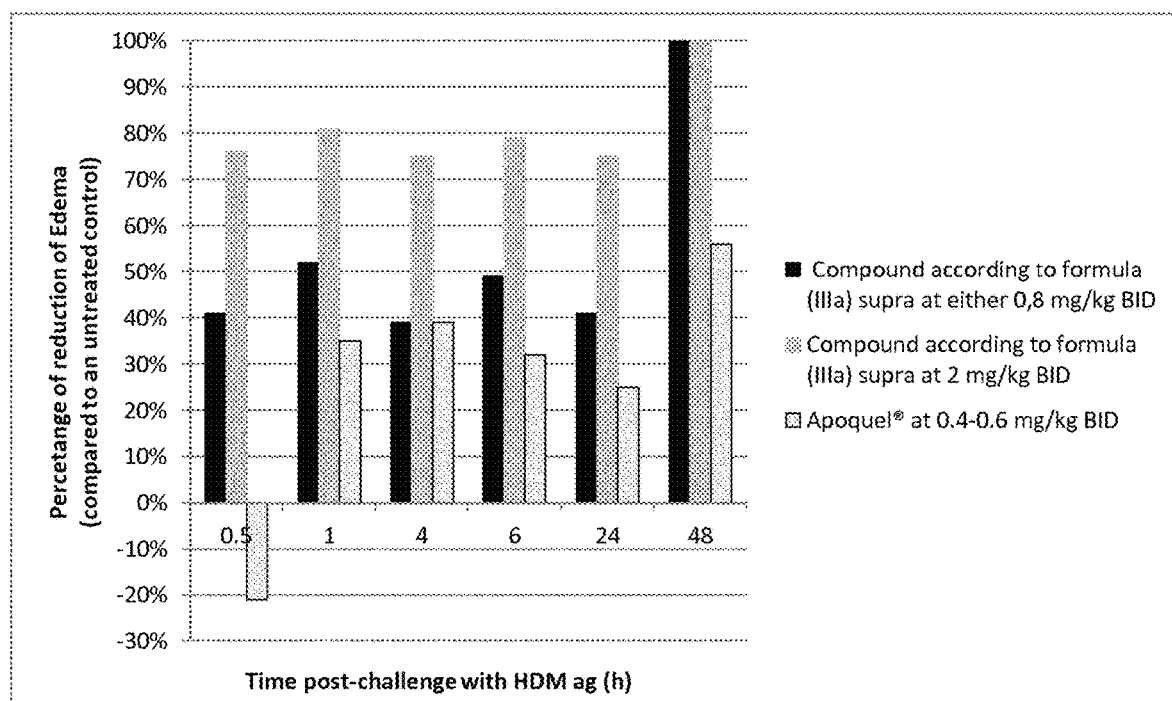
FIG. 2 shows a comparative reduction of edema in the CAD model (expressed as % compared the control group) after treatment of up to >75% when administered at 2 mg/kg BID with a compound of formula (IIIa).

These results show that the compound according to formula (IIIa) supra achieves a comparative reduction of edema in the CAD model (expressed as % compared the control group) after treatment of up to >75% when administered at 2 mg/kg BID (FIG. 2).

The invention claimed is:

1. A method for the treatment and/or prophylaxis of allergic and/or inflammatory diseases in domestic animals and/or in farm animals in need thereof comprising administering to the animal an effective amount of the compound of the general formula (I)

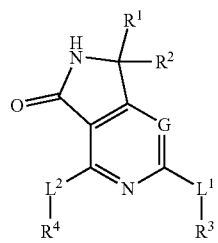

wherein:
G is selected from N and $C(R^5)$;
$L^1$ and $L^2$ are each independently selected from —NH— and a bond;
$R^1$ and $R^2$ are each independently selected from hydrogen, halogen, $C_{1-3}$-alkyl, and $C_{1-3}$-halogenoalkyl having 1 to 5 halogen atoms, or $R^1$ and $R^2$, together with the atom to which they are attached, form a $C_{3-6}$-cycloalkyl;
$R^3$ is selected from $C_{2-6}$-alkyl, $C_{3-8}$-cycloalkyl, $C_{2-5}$-heterocyclyl, and $C_{1-9}$-heteroaryl, each optionally substituted with one to five substituents independently selected from halogen, oxo, —$NO_2$, —CN, $R^6$ and $R^7$;
$R^4$ is selected from $C_{3-8}$-cycloalkyl, $C_{2-5}$-heterocyclyl, $C_{6-14}$-aryl and $C_{1-9}$-heteroaryl, each optionally substituted with one to five substituents independently selected from halogen, oxo, —CN, $R^6$ and $R^7$;
$R^5$ is selected from hydrogen, halogen, —CN, $C_{1-4}$-alkyl, $C_{2-4}$-alkenyl, $C_{2-4}$-alkynyl, $C_{2-5}$-heterocyclyl, $C_{1-5}$-heteroaryl, and $R^{10}$, wherein the alkyl, alkenyl, alkynyl moieties are each optionally substituted with one to five substituents independently selected from halogen, —CN, oxo, and $R^{10}$, and wherein the heterocyclyl moiety has 3 to 6 ring atoms and the heteroaryl moiety has 5 or 6 ring atoms, and the heterocyclyl and heteroaryl moieties are each optionally substituted with one to four substituents independently selected from halogen, —NO, —CN, $C_{1-4}$-alkyl, $C_{2-4}$-alkenyl, $C_{2-4}$-alkynyl, $C_{1-4}$-halogenoalkyl having 1 to 5 halogen atoms, and $R^{10}$;
each $R^6$ is independently selected from —$OR^8$, —$N(R^8)R^9$, —$NR^8C(O)R^9$, —$C(O)R^8$, —$C(O)OR^8$, —$C(O)N(R^8)R^9$, —$C(O)N(R^8)OR^9$, —$C(O)N(R^8)S(O)_2R^9$, —$N(R^8)S(O)_2R^9$, —$S(O)_nR^8$, and —$S(O)_2N(R^8)R^9$;
each $R^7$ is independently selected from $C_{1-6}$-alkyl, $C_{2-6}$-alkenyl, $C_{2-6}$-alkynyl, $C_{3-6}$-cycloalkyl-$(CH_2)_m$-, $C_{6-14}$-aryl-$(CH_2)_m$-, $C_{2-5}$-heterocyclyl-$(CH_2)_m$-, and $C_{1-9}$-heteroaryl-$(CH_2)_m$-, each optionally substituted with one to five substituents independently selected from halogen, oxo, —CN, $C_{1-6}$-alkyl, $C_{1-6}$-halogenoalkyl having 1 to 5 halogen atoms, and $R^{10}$;
each $R^8$ and $R^9$ is independently selected from hydrogen or from $C_{1-6}$-alkyl, $C_{2-6}$-alkenyl, $C_{2-6}$-alkynyl, $C_{3-6}$-cycloalkyl-$(CH_2)_m$-, $C_{6-14}$-aryl-$(CH_2)_m$-, $C_{2-5}$-heterocyclyl-$(CH_2)_m$- and $C_{1-9}$-heteroaryl-$(CH_2)_m$-, each optionally substituted with one to five substituents independently selected from halogen, oxo, —$NO_2$, —CN, $C_{1-6}$-alkyl, $C_{1-6}$-halogenoalkyl having 1 to 5 halogen atoms, and $R^{10}$;
each $R^{10}$ is independently selected from —$OR^{11}$, —$N(R)R^{12}$, —$N(R^{11})C(O)R^{12}$, —$C(O)OR^{11}$, —$C(O)N(R^{11})R^{12}$, —$C(O)N(R^{11})OR^{12}$, —$C(O)N(R^{11})S(O)_2R^{12}$, —$NR^{11}S(O)_2R^{12}$, —$S(O)_nR^{11}$, and —$S(O)_2N(R^{11})R^{12}$,
each $R^{11}$ and $R^{12}$ is independently selected from hydrogen and $C_{1-6}$-alkyl;
each n is independently selected from 0, 1 and 2; and
each m is independently selected from 0, 1, 2, 3, and 4;
wherein each of the aforementioned heteroaryl moieties has one to four heteroatoms independently selected from N, O, and S, and each of the aforementioned heterocyclyl moieties is saturated or partially unsaturated and has one or two heteroatoms independently selected from N, O, and S;
and the diastereomers, enantiomers, salts, solvates or solvates of the salts thereof, wherein the inflammatory disease is atopic dermatitis, Flea Allergy Dermatitis, inflammatory pain, non-infectious recurrent airway disease, insect hypersensitivity, asthma, respiratory disease, mastitis or endometritis.

2. The method according to claim 1, wherein the disorder is Atopic Dermatitis and Flea Allergy Dermatitis in dogs or cats.

3. The method of claim 1, wherein the effective amount of the compound is administered to an animal in need thereof in a composition comprising an inert, non-toxic, pharmaceutically suitable excipient.

4. The method according to claim 3 wherein the disease is Canine Atopic Dermatitis, and wherein symptoms selected from the group consisting of itching, excessive scratching, rubbing on the carpet, hair loss (alopecia), greasy or flaky skin with a foul odor, and excessive chewing on the paws groin and/or armpits are reduced upon treatment.

5. A method for treatment and/or prevention of allergic and/or inflammatory diseases in animals comprising administering and effective amount of a dual SYK and JAK, SYK and IRAK4, or JAK and IRAK4 inhibitor to a domestic animals and/or farm animal in need thereof.

6. The method according to claim 1, wherein G is $C(R^5)$, with $R^5$ and/or wherein $L^1$ is —NH— and/or wherein $L^2$ is a bond, or the diastereomers, enantiomers, metabolites, salts, solvates or solvates of the salts thereof.

7. The method according to claim 1 wherein $R^1$ and $R^2$ are both hydrogen.

8. The method according to claim 1, wherein $R^3$ is 2-amino-$C_{3-8}$-cycloalk-1-yl, preferably 2-amino-cyclohex-1-yl, optionally substituted with one to four substituents independently selected from halogen, oxo, —$NO_2$, —CN, $R^6$, and $R^7$.

9. The method according to claim 1 wherein $R^4$ is a monocyclic C2-4-heteroaryl, preferably pyrazol-4-yl, optionally substituted with one to four substituents independently selected from halogen, oxo, —CN, $R^6$, and $R^7$.

10. The method according to claim 1, wherein $R^4$ is substituted with methyl, ethyl, cyclopropyl or $C_{1-2}$-halogenoalkyl having 1 to 5 halogen atoms.

11. The method according to claim 1, wherein the compound is (III) or (IIIa)

(III)

(IIIa)

12. The method according to claim 1, wherein the compound is (IV) or (IVa)

(IV)

(IVa)

13. The method of claim 11 wherein the disease is Canine Atopic Dermatitis, and wherein symptoms selected from the group consisting of itching, excessive scratching, rubbing on the carpet, hair loss (alopecia), greasy or flaky skin with a foul odor, and excessive chewing on the paws groin and/or armpits are reduced upon treatment.

14. The method according to claim 12, wherein the disease is Canine Atopic Dermatitis, and wherein symptoms selected from the group consisting of itching, excessive scratching, rubbing on the carpet, hair loss (alopecia), greasy or flaky skin with a foul odor, and excessive chewing on the paws groin and/or armpits are reduced upon treatment.

15. The method of claim 1, comprising administering to the animal comprising administering to the animal an effective amount of the compound of the general formula (I)

(I)

wherein:
G is $C(R^5)$;
$L^1$ and $L^2$ are each independently selected from —NH— and a bond;
$R^1$ and $R^2$ are each hydrogen;
$R^3$ is $C_{3-8}$-cycloalkyl or $C_{2-5}$-heterocyclyl optionally substituted with one to five substituents independently selected from halogen, oxo, —$NO_2$, —CN, or $NH_2$;
$R^4$ is selected from $C_{3-8}$-cycloalkyl or $C_{2-5}$-heterocyclyl, each optionally substituted with one to five substituents independently selected from halogen, oxo, —CN, or $NH_2$;

$R^4$ is selected from $C_{3-8}$-cycloalkyl, $C_{2-5}$-heterocyclyl, $C_{6-14}$-aryl and $C_{1-9}$-heteroaryl, each optionally substituted with one to five substituents independently selected from halogen, oxo, —CN, $C_{1-6}$-alkyl, $C_{2-6}$-alkenyl, or $C_{2-6}$-alkynyl; and
$R^5$ is halogen.

* * * * *